(12) United States Patent
Wada et al.

(10) Patent No.: US 6,720,424 B1
(45) Date of Patent: Apr. 13, 2004

(54) AMINOBENZOIC ACID DERIVATIVES

(75) Inventors: Hisaya Wada, Tokyo (JP); Hajime Asanuma, Tokyo (JP); Tetsuo Takayama, Tokyo (JP); Masakazu Sato, Tokyo (JP); Takehiro Yamagishi, Tokyo (JP); Masabumi Shibuya, Kawaguchi (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 149 days.

(21) Appl. No.: 10/019,525

(22) PCT Filed: Jul. 3, 2000

(86) PCT No.: PCT/JP00/04406

§ 371 (c)(1), (2), (4) Date: Jan. 2, 2002

(87) PCT Pub. No.: WO01/02344

PCT Pub. Date: Jan. 11, 2001

(30) Foreign Application Priority Data

Jul. 1, 1999 (JP) ............................................. 11-188271
Jul. 1, 1999 (JP) ............................................. 11-188272

(51) Int. Cl.$^7$ ..................... C07D 211/72; C07C 229/00; C07C 303/00
(52) U.S. Cl. .................. 546/291; 546/304; 560/19; 562/433; 564/84; 564/85; 564/88
(58) Field of Search .................... 546/291, 304; 560/19; 562/433; 564/84, 85, 88

(56) References Cited

U.S. PATENT DOCUMENTS

| | | | |
|---|---|---|---|
| 5,872,280 A | * | 2/1999 | Abram et al. ................ 562/430 |
| 6,090,480 A | * | 7/2000 | Hayashi ........................ 428/332 |
| 6,436,925 B1 | * | 8/2002 | Lubisch et al. ........... 514/217.2 |
| 6,534,513 B1 | * | 3/2003 | Porter et al. ................. 514/277 |

FOREIGN PATENT DOCUMENTS

| | | |
|---|---|---|
| EP | 0 791 576 A2 | 8/1997 |
| EP | 0 894 496 A1 | 2/1999 |
| JP | 10-259176 A | 9/1998 |
| JP | 11-40038 A | 5/1999 |
| WO | WO 97/29744 A1 | 8/1997 |

OTHER PUBLICATIONS

International Search Report, 2001.

\* cited by examiner

*Primary Examiner*—Deborah C. Lambkin
(74) *Attorney, Agent, or Firm*—Sughrue Mion, PLLC

(57) ABSTRACT

Aminobenzoic acid derivatives represented by Formula (1) as follows:

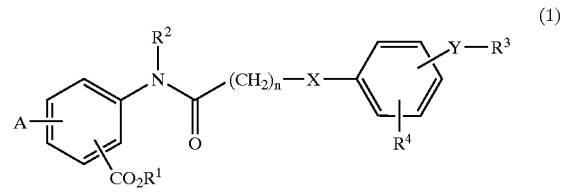

(wherein, $R^1$ represents a hydrogen atom, a $C_{1-6}$alkyl group, or the like; $R^2$ represents a hydrogen atom, a $C_{1-6}$alkyl group, or the like; $R^3$ represents a $C_{8-25}$alkyl group, or the like; $R^4$ represents a hydrogen atom or a group represented by $OR^9$ or $CO_2R^{10}$ (wherein $R^9$ and $R^{10}$ represent a hydrogen atom or a $C_{1-6}$ alkyl group); A represents a group represented by $S(O)_qR^{15}$ (wherein q is 0, 1, or 2, $R^{15}$ represents a $C_{1-6}$alkyl group, a phenyl $C_{1-3}$alkyl group, or a group represented by $(CH_2)_mOR^{16}$ (wherein m is 2 or 3, and $R^{16}$ represents a hydrogen atom or a methoxymethyl group), or the like; X represents O, a single bond, CH=CH, or a group represented by $NR^{27}$ (wherein $R^{27}$ represents a hydrogen atom or a t-butoxycarbonyl group); Y represents O, CONH, NHCO, or a group represented by $NR^{28}$ (wherein $R^{28}$ represents a hydrogen atom or a t-butoxycarbonyl group); and n is an integer of 0 to 15)
or pharmaceutically acceptable salts of the same are employed as VEGF receptor antagonists, and in particular as therapeutic agents for the diseases in which VEGF is involved.

13 Claims, No Drawings

AMINOBENZOIC ACID DERIVATIVES

This application is a 371 of PCT/JP00/04406 Jul. 3, 2000.

TECHNICAL FIELD

The present invention relates to VEGF-receptor antagonists inhibiting VEGF, which corresponds to specific growth factors of vascular endothelial cells, from binding to receptors.

The present application is based on patent applications in Japan (Japanese Patent Application No. Hei 11-188271 and Japanese Patent Application No. Hei 11-188272), the disclosure of which is incorporated herein by reference as a part of the present description.

BACKGROUND ART

VEGF (vascular endothelial growth factor) is a growth factor exhibiting extremely high specificity to vascular endothelial cells. VEGF and the receptors thereof play main roles in physiologic angiogenesis such as placentation or development. As VEGF receptors, Flt-1 (fms-like tyrosine kinase) and KDR (kinase insert domain containing receptor) have been reported (*Advances in Cancer Research*, vol. 67, pp. 281–316, 1995).

It is suggested that VEGF and the receptors thereof play main roles not only in physiologic angiogenesis but also in pathologic angiogenesis observed in diseases such as diabetic retinopathy, chronic rheumatism, and solid tumors (*Advances in Cancer Research*, vol. 67, pp. 281–316, 1995), and are involved in progress of these diseases. In addition, it is known that VEGF and the receptors thereof are involved not only in angiogenesis but also in vascular hyperpermeability. It is suggested that vascular hyperpermeability due to VEGF is involved in pathologic symptoms such as carcinomatous ascites retention or cerebral edema upon ischemia reperfusion injury (*J. Clin. Invest.*, vol. 104, pp. 1613–1620, 1999).

Therefore, it is believed that substances which inhibit binding between VEGF and the receptors thereof are considered to be useful in treatment of various diseases in which pathologic angiogenesis due to VEGF is involved, and amelioration of pathologic symptoms in which vascular hyperpermeability due to VEGF is involved.

DISCLOSURE OF THE INVENTION

An objective of the present invention is to provide compounds for use as a VEGF-receptor antagonist for treating diseases in which angiogenesis induced by VEGF is involved, and for ameliorating pathologic symptoms in which vascular hyperpermeability induced by VEGF is involved.

The compounds according to the present invention correspond to aminobenzoic acid derivatives represented by Formula (1) as follows:

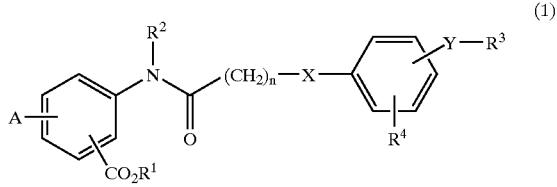

{in Formula (1), $R^1$ represents a hydrogen atom or a $C_{1-6}$alkyl group;

$R^2$ represents a hydrogen atom, a $C_{1-6}$alkyl group, a $C_{3-8}$ cycloalkyl $C_{1-3}$alkyl group, a phenyl $C_{1-3}$alkyl group, a group represented by $CH_2CO_2R^5$ (wherein $R^5$ represents a hydrogen atom or a $C_{1-6}$alkyl group), or a group represented by $CH_2CON(R^6)R^7$ (wherein $R^6$ and $R^7$ independently represent a hydrogen atom or a $C_{1-6}$alkyl group);

$R^3$ represents a $C_{8-25}$alkyl group, a group represented by $(CH_2)_pCO_2R^{11}$ (wherein p is an integer of 1 to 20, and $R^{11}$ represents a hydrogen atom or a $C_{1-6}$alkyl group), or a group represented by $(CH_2)_3CONHCH(R^{12})CONHR^{13}$ (wherein $R^{12}$ represents a hydrogen atom or a group represented by $CH_2CO_2R^{14}$ group (wherein $R^{14}$ represents a hydrogen atom or a $C_{1-6}$alkyl group), and $R^{13}$ represents a $C_{1-20}$alkyl group);

$R^4$ represents a hydrogen atom or a group represented by $OR^9$ or $CO_2R^{10}$ (wherein $R^9$ and $R^{10}$ independently represent a hydrogen atom or a $C_{1-6}$alkyl group), A represents a group represented by $S(O)_qR^{15}$ (wherein q is 0, 1, or 2, $R^{15}$ represents a $C_{1-6}$alkyl group, a phenyl $C_{1-3}$ alkyl group, or a group represented by $(CH_2)_mOR^{16}$ (wherein m is 2 or 3, and $R^{16}$ represents a hydrogen atom or a methoxymethyl group)), a group represented by Formula (2) as follows:

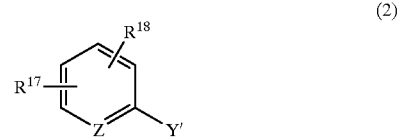

(in the formula, $R^{17}$ represents a hydrogen atom or a group represented by $CO_2R^{19}$, $CH_2CO_2R^{20}$, $CH_2CH_2CO_2R^{21}$, or $CH=CHCO_2R^{22}$ (wherein $R^{19}$, $R^{20}$, $R^{21}$, and $R^{22}$ independently represent a hydrogen atom or a $C_{1-6}$alkyl group), $R^{18}$ represents a hydrogen atom or a group represented by $CO_2R^{23}$ (wherein $R^{23}$ represents a hydrogen atom or a $C_{1-6}$alkyl group), Y' represents O, S, or $NR^{24}$ (wherein $R^{24}$ represents a hydrogen atom or a $C_{1-6}$alkyl group), and Z represents CH or N), or a group represented by Formula (3) as follows:

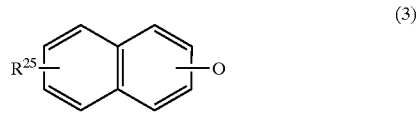

(in the formula, $R^{25}$ represents a hydrogen atom or a group represented by $CO_2R^{26}$ (wherein $R^{26}$ represents a hydrogen atom or a $C_{1-6}$alkyl group));

X represents O, a single bond, or a group represented by $NR^{27}$ (wherein $R^{27}$ represents a hydrogen atom or a t-butoxycarbonyl group);

Y represents O, CONH, NHCO, or a group represented by NR$^{28}$ (wherein R$^{28}$ represents a hydrogen atom or a t-butoxycarbonyl group, with the proviso that when Y represents NHCO, A is not represented by Formula (2) described above); and n is an integer of 0 to 15}
or pharmaceutically acceptable salt of the same.

BEST MODE FOR CARRYING OUT THE INVENTION

In the present invention, the term "$C_{1-6}$alkyl group" means a straight-chain or branched-chain alkyl group having 1 to 6 carbon atoms. As examples thereof, mention may be made of, for example, a methyl group, an ethyl group, a propyl group, an isopropyl group, a butyl group, an isobutyl group, a t-butyl group, a pentyl group, an isopentyl group, a 1-ethylpropyl group, a hexyl group, an isohexyl group, a 1-ethylbutyl group, and the like. The term "$C_{3-8}$cycloalkyl $C_{1-3}$alkyl group" means a straight-chain or branched-chain alkyl group having 1 to 3 carbon atoms, substituted with a cycloalkyl group having 3 to 8 carbon atoms. As examples thereof, mention may be made of, for example, a cyclopropylmethyl group, a cyclobutylmethyl group, a cyclopentylmethyl group, and the like.

The term "$C_{8-25}$alkyl group" means a straight-chain or branched-chain alkyl group having 8 to 25 carbon atoms. As examples thereof, mention may be made of an octyl group, a 7-methyloctyl group, a 7,7-dimethyloctyl group, an octadecyl group, a 17-methyloctadecyl group, a 17,17-dimethyloctadecyl group, a pentacosyl group, a 23-methyltetracosyl group, a 22,22-dimethyltricosyl group, and the like.

The term "$C_{1-20}$alkyl group" means a straight-chain or branched-chain alkyl group having 1 to 20 carbon atoms. As examples thereof, mention may be made of, for example, a methyl group, an ethyl group, a decyl group, a 9-methyldecyl group, a 9,9-dimethyldecyl group, an icosyl group, and the like.

The term "phenyl $C_{1-3}$alkyl group" means a straight-chain or branched-chain alkyl group having 1 to 3 carbon atoms, substituted with a phenyl group. As examples thereof, mention may be made of, for example, a benzyl group, a 2-phenylethyl group, a 3-phenylpropyl group, and the like.

In addition, as examples of the pharmaceutically acceptable salt in the present invention, mention may be made of, for example, a salt with an inorganic acid such as sulfuric acid, hydrochloric acid, or phosphoric acid, or the like; a salt with an organic acid such as acetic acid, oxalic acid, lactic acid, tartaric acid, fumaric acid, maleic acid, methanesulfonic acid, benzenesulfonic acid, or the like; a salt with an amine such as trimethylamine, methylamine, or the like; a salt with a metal ion such as sodium ion, potassium ion, calcium ion, or the like; and the like.

In addition, some of the compounds according to the present invention exhibit crystal polymorphism. The present invention includes any crystal forms thereof.

In Formula (1), it is preferable that A represent a group represented by S(O)$_q$R$^{15}$ (wherein q and R$^{15}$ have the same meanings as described above) or a group represented by Formula (5) as follows:

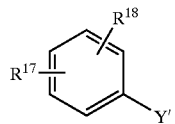

(in the formula, R$^{17}$ R$^{18}$, and Y' have the same meanings as described above), and it is more preferable that A represent a group represented by SR$^{15}$ (wherein R$^{15}$ has the same meaning as described above) or a group represented by Formula (5) wherein R$^{17}$ represents CO$_2$R$^{19}$ (wherein R$^{19}$ has the same meaning as described above) and R$^{18}$ represents a hydrogen atom. In addition, it is most preferable that A represent a group represented by SR$^{15}$ (wherein R$^{15}$ represents a $C_{1-6}$alkyl group) or a group represented by Formula (5) wherein R$^{17}$ represents CO$_2$H and R$^{18}$ represents a hydrogen atom.

In addition, in Formula (1), R$^2$ preferably presents a hydrogen atom or a $C_{1-6}$alkyl group.

In Formula (1), R$^3$ preferably represents a straight-chain or branched-chain alkyl group having 8 to 25 carbon atoms, and more preferably represents an alkyl group having 14 to 22 carbon atoms, and most preferably represents an alkyl group having 18 carbon atoms.

In Formula (1), it is preferable that R$^4$ represents a hydrogen atom.

In Formula (1), it is preferable that a CO$_2$R$^1$ group is located at the position as shown in Formula (4) as follows:

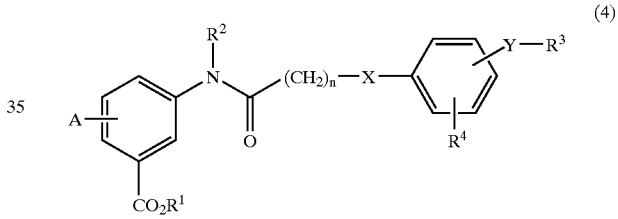

and it is preferable that A in Formula (4) is located at the position as shown in Formula (6) as follows:

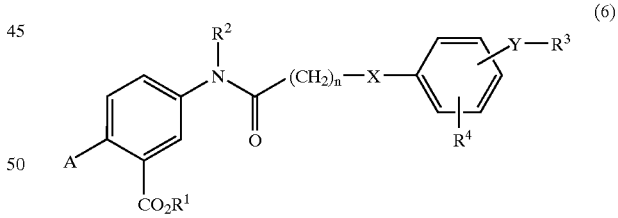

In addition, it is preferable that X represents O or a single bond, and it is more preferable that X represents a single bond.

It is preferable that Y represents O. It is preferable that n is 1 or 2.

Therefore, the preferable compounds in the present invention are selected from those having combinations of the preferable substituents described above.

The compounds of the present invention can be produced according to the reactions described below.

1) Case in Which a Represents a Group Represented by S(O)$_q$R$^{15}$

The symbols in the formula have the same meanings as described above. A' represents S(O)$_q$R$^{15}$; halo means a halogen atom; R represents $R^2$ excluding a hydrogen atom; R' represents a t-butyl group, a p-methoxybenzyl group, or a diphenylmethyl group; and R" represents a lower alkyl group.

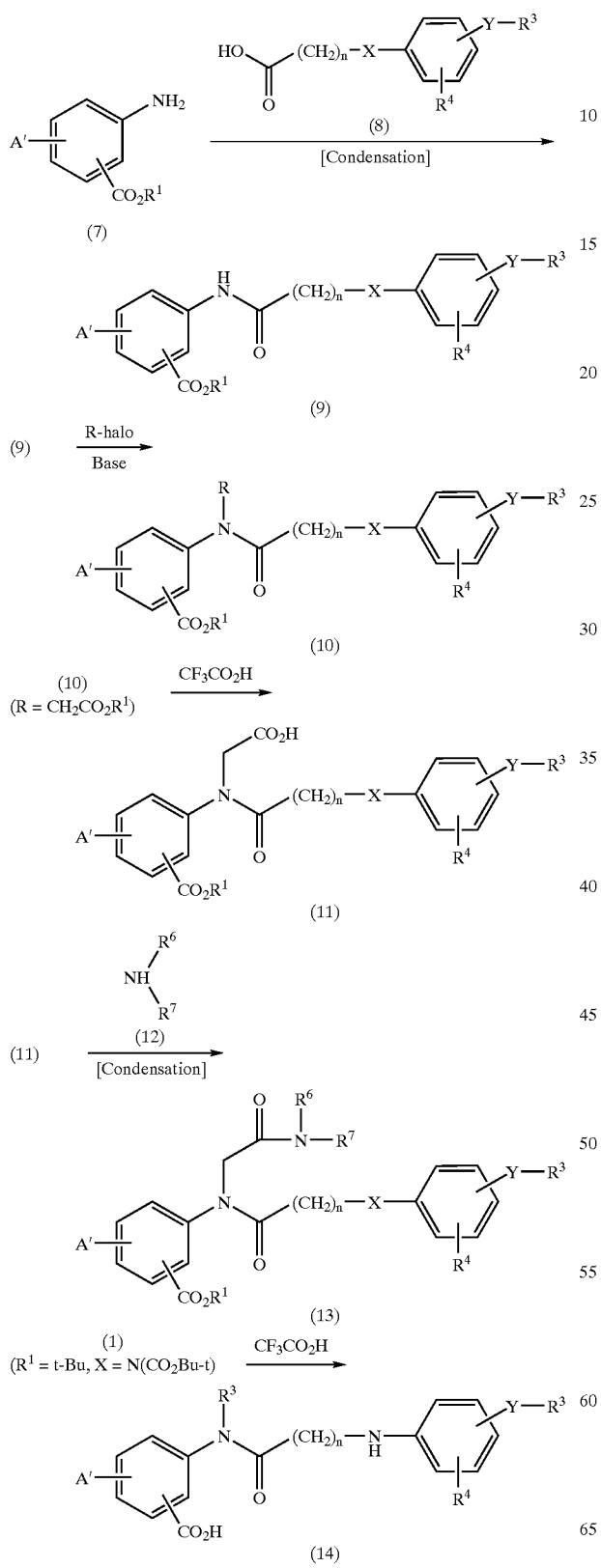

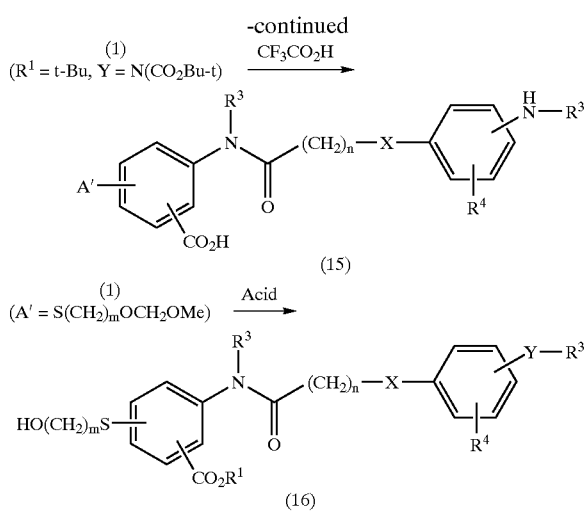

A compound represented by Formula (9) according to the present invention is prepared by condensation between a compound of Formula (7) and a carboxylic acid compound of Formula (8). As the condensing agent, there can be employed the condensing agents commonly used when amides are produced by amines and carboxylic acids, such as 1-(3-(dimethylamino)propyl)-3-ethylcarbodiimide hydrochloride and 1-hydroxybenzotriazole. As the solvent, inert solvents such as N,N-dimethylformamide and the like can be employed. The compound of the present invention of Formula (9) can be also produced by converting the carboxylic acid of Formula (8) into an acid halide or a mixed anhydride according to a common method, followed by a reaction with the compound of Formula (7) in the presence of a base. As the base, pyridine, triethylamine, or the like may be employed. As examples of the solvent, mention may be made of inert solvents such as methylene chloride and the like.

A compound of Formula (10) according to the present invention in which the nitrogen atom of the amide group is modified (by R) can be produced by carrying out a substitution of the hydrogen atom of the amide group in the compound of Formula (9) in the presence of a strong base. In this reaction, as examples of the base, mention may be made of sodium hydride, potassium hydride, calcium hydride, and the like. As the solvent, inert solvents such as N,N-dimethylformamide and the like can be employed.

Among these compounds of Formula (10), a compound having $CH_2CO_2R'$ as R can be converted into a carboxylic acid compound of Formula (11), by a reaction in the presence of a strong acid such as trifluoroacetic acid or the like in an inert solvent such as methylene chloride or the like.

The carboxylic acid compound of Formula (11) can react with an amine of Formula (12) in the presence of a condensing agent to yield an amide compound of Formula (13). As the condensing agent, there can be employed the condensing agents commonly used when amides are produced by amines and carboxylic acids, such as 1-(3-(dimethylamino)propyl)-3-ethylcarbodiimide hydrochloride and 1-hydroxybenzotriazole. As the solvent, inert solvents such as N,N-dimethylformamide and the like can be employed.

A compound of Formula (14) can be produced by reacting a compound of Formula (1) in which $R^1$ represents t-Bu and X represents $N(CO_2Bu-t)$ in the presence of a strong acid such as trifluoroacetic acid in an inert solvent such as methylene chloride.

A compound of Formula (15) can be produced by reacting a compound of Formula (1) in which $R^1$ represents t-Bu and X represents $N(CO_2Bu-t)$ in the presence of a strong acid such as trifluoroacetic acid in an inert solvent such as methylene chloride.

A compound of Formula (16) can be produced by reacting a compound of Formula (1) in which A' represents $S(CH_2)_mOCH_2OMe$ in the presence of an acid such as hydrochloric acid, sulfuric acid, acetic acid, trifluoroacetic acid, or the like in a solvent mixture of a lower alcohol such as methanol and a polar solvent such as tetrahydrofuran.

The compounds of the present invention in which $R^1$ represents an alkyl group, $R^4$ represents an alkoxycarbonyl group, or $R^3$ represents an alkoxycarbonylalkyl group can yield the compounds of the present invention in which $R^1$ represents a hydrogen atom, $R^4$ represents a carboxyl group, or $R^3$ represents a carboxyalkyl group, respectively, according to the common methods of hydrolysis in which an ester group is subjected to a hydrolysis.

In addition, the compounds of the present invention in which A' represents $SR^{15}$ can yield the compounds of the present invention in which A' represents $SOR^{15}$ or $SO_2R^{15}$, by an oxidation with an oxidant such as m-chloroperoxybenzoic acid or the like in an inert solvent such as methylene chloride or the like.

2) Case in Which A Represents a Group Represented by Formula (2) or Formula (3)

As an example, a case in which A in Formula (1) described above represents a group represented by Formula (2) is described. The symbols in the formulae have the same meanings as described above, and "halo" represents a halogen atom and R represents $R^2$ excluding a hydrogen atom.

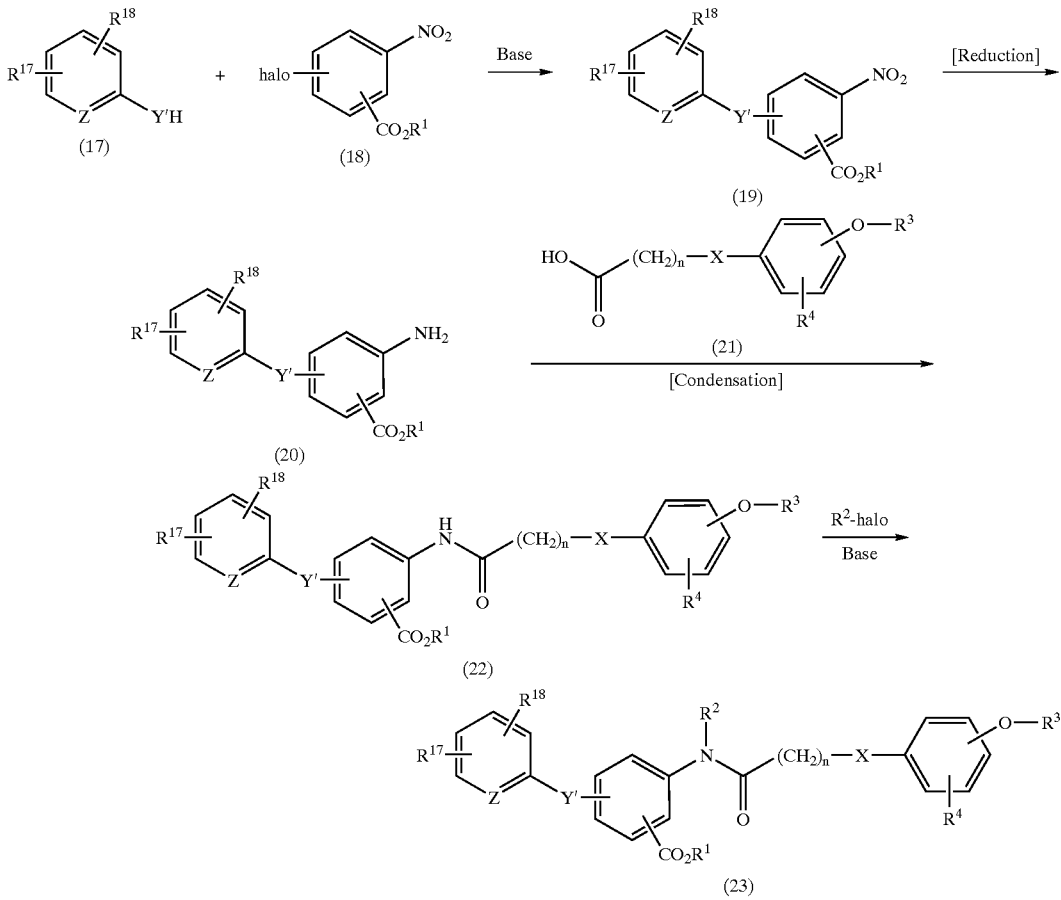

A compound of Formula (17) and a nitro compound of Formula (18) are stirred in the presence of a base and in the presence or absence of a catalytic amount of copper powders in an appropriate solvent at temperatures of 0° C. to 150° C., to yield a compound of Formula (19). As the base, there can be employed inorganic bases such as potassium carbonate, sodium carbonate, sodium hydrogencarbonate, potassium hydrogencarbonate, cesium carbonate, sodium hydride, potassium hydride, and the like; organic bases such as triethylamine, diisopropylethylamine, pyridine, and the like; or the like. As the solvent, an inert solvent such as N,N-dimethylformamide or the like can be employed.

According to need, the compound of Formula (19) is stirred with a lower alkyl halide in the presence of a base in an appropriate solvent at temperatures of 0° C. to 100° C. to yield the compound of Formula (19) in which $R^{17}$ represents a hydrogen atom or a group including an alkoxycarbonyl group, $R^{18}$ represents a hydrogen atom or an alkoxycarbonyl group, and $R^1$ represents an alkyl group. As the base, potassium carbonate, sodium carbonate, sodium hydrogencarbonate, potassium hydrogencarbonate, cesium carbonate, or the like can be employed. As the solvent, an inert solvent such as N,N-dimethylformamide or the like can be employed.

Subsequently, the nitro group in the compound of Formula (19) which does not include a carboxyl group is reduced to an amino group to yield a compound of Formula (20). As examples of the reduction method, mention may be made of a reduction using a metal such as iron or tin or a metal salt in the presence of an acid such as acetic acid or hydrochloric acid and ammonium chloride; a catalytic hydrogenation using a catalyst such as palladium/carbon, Raney nickel, platinum oxide, or the like; a reduction using ammonium formate in the presence of a palladium/carbon catalyst; or the like. As examples of the solvent, mention may be made of inert solvents such as methanol, ethanol, isopropyl alcohol, and the like.

The compound of Formula (20) obtained herein is condensed with a carboxylic acid of Formula (21) to yield a compound of Formula (22) of the present invention. As the condensing agent, there can be employed the condensing agents commonly used when amides are produced by amines and carboxylic acids, such as 1-(3-(dimethylamino) propyl)-3-ethylcarbodiimide hydrochloride and 1-hydroxybenzotriazole. As the solvent, inert solvents such as N,N-dimethylformamide and the like can be employed. Alternatively, the compound of Formula (22) can be prepared by converting the carboxylic acid of Formula (21) into an acid halide or a mixed anhydride according to a common method, followed by a reaction with the compound of Formula (20) in the presence of a base. As the base, pyridine, triethylamine, or the like can be employed. As the solvent, an inert solvent such as methylene chloride or the like may be mentioned.

Alkylation of the compound of Formula (22) is carried out in the presence of a strong base, to yield a compound (23) of the present invention in which the nitrogen atom of the amide is alkylated. In the case of the compounds of Formula (22) in which Y' represents NH, the compounds of the present invention in which $R^2$ represents an alkyl group, and Y' represents an N-alkyl group can be yielded. As examples of the base herein, mention may be made of sodium hydride, potassium hydride, calcium hydride, and the like. As the solvent, an inert solvent such as N,N-dimethylformamide or the like can be employed.

The compounds of Formula (22) and Formula (23) in which $R^1$ represents an alkyl group, $R^{17}$ represents a hydrogen atom or a group including an alkoxycarbonyl group, and $R^{18}$ represents a hydrogen atom or an alkoxycarbonyl group can respectively yield the compounds of the present invention in which $R^1$ represents a hydrogen atom, $R^{17}$ represents a hydrogen atom or a group including a carboxyl group, and $R^{18}$ represents a hydrogen atom or a carboxyl group, according to the common methods of hydrolysis in which an ester group is subjected to a hydrolysis.

The compounds of the present invention in which A of Formula (1) described above represents a group represented by Formula (3) can be prepared according to the same operations as described in the preparation methods for the compounds in which Y in the groups represented by Formula (2) represents O.

The compounds represented by Formula (1) or pharmaceutically acceptable salts of the same are employed as the VEGF-receptor antagonists described above, and in particular, as therapeutic agents of the diseases in which VEGF is involved, and are employed in manufacture thereof. The VEGF-receptor antagonists of the present invention inhibit proliferation of VEGF-dependent vascular endothelial cells by inhibiting binding between the ligands (VEGF) and the VEGF receptors to inhibit angiogenesis, as well as inhibit vascular hyperpermeability due to VEGF.

Herein, as examples of diseases and pathologic symptoms in which VEGF is involved, mention may be made of diabetic retinopathy and other retinopathies, chronic rheumatism, solid tumors, ischemia-reperfusion-injury related cerebral edema and damage, psoriasis, atherosclerosis, retrolental fibroplasia, neovascular glaucoma, age-related macular degeneration, thyroid gland hyperplasia (including Graves' disease), chronic inflammation, pneumonia, nephrotic syndrome, tumor immune hypofunction, ascites retention, pericardial effusion (those relating to pericarditis, and the like), retention of pleural effusion, and the like.

Among these, in particular, in the diseases described below, ameliorations in pathologies by inhibition of VEGF have been reported.

(1) Diabetic Retinopathy and Other Retinopathies

Diabetic retinopathy refers to diseases in which various lesions form in the retina or vitreous body due to abnormalities in retinal blood vessels, caused by exposure under hyperglycaemic conditions for a long period of time. It is known that according to progress of the disease, abnormal angiogenesis and bleeding in the eyeball lead to blindness. In addition, it is reported that there is a positive correlation relationship between increasing in VEGF level in the eyeball and abnormal angiogenesis in the eyeball (*New Engl. J. Med.*, vol. 331, pp. 1480–1487, 1994). In addition, it is reported that in a retinopathy model of a monkey, by intraocular administration of an anti-VEGF neutralizing monoclonal antibody, VEGF activities are inhibited to result in inhibition of angiogenesis (*Arch. Opthalmol.*, vol. 114, pp. 66–71, 1996), and that in a retinopathy model of a mouse, by administration of an inhibitor of VEGF signal transduction, retinal angiogenesis is inhibited (*Am. J. Pathol.*, vol. 156, pp. 697–707, 2000). As described above, it may be understood that VEGF-receptor antagonists are effective on diabetic retinopathy and other retinopathies.

(2) Chronic Rheumatism

It is reported that the serum VEGF values of patients suffering from chronic rheumatism are significantly higher as compared to those of healthy persons, and in nidal regions, production of VEGF is increased (*J. Immunol.*, vol. 152, pp. 4149–4156, 1994), and it is suggested that VEGF is greatly involved in formation of diseases. In addition, in a collagen arthritis model of mouse, ameliorating actions for diseases by administration of an anti-VEGF antiserum are reported (*J. Immunol.*, vol. 164, pp. 5922–5927, 2000).

(3) Solid Tumors

It is believed that VEGF plays important roles in angiogenesis in malignant tumors (*Biochem. Biophys. Res. Commun.*, vol. 161, pp. 851–858, 1989).

It is known that production of VEGF is increased in cerebral tumors such as gliomas, malignant lymphomas, pituitary adenomas, meningiomas, and the like, various solid malignant tumors such as melanomas, colon cancers, ovarian cancers, pancreatic cancers, esophageal cancers, rhabdomyosarcomas, leiomyosarcomas, Kaposi's sarcoma, lung cancers, and the like (*Nature*, vol. 362, pp. 841–844, 1993; *Biochem. Biophys. Res. Commun.*, vol. 183, pp. 1167–1174, 1992). It is believed that VEGF secreted from tumor cells causes proliferation of vascular endothelial cells by binding to tyrosine-kinase-type receptors which are specifically present in vascular endothelial cells, and are involved in proliferation or metastasis of tumors due to induction of tumor angiogenesis (*Oncogene*, vol. 5, pp. 519–524, 1990; *Science*, vol. 255, pp. 989–991, 1992).

It is reported that tumor proliferation can be inhibited by administration of an anti-VEGF monoclonal antibody in an implantation model in the nude mouse of glioblastoma, rhabdomyosarcoma, and leiomyosarcoma (*Nature*, vol. 362, pp. 841–844, 1993), and it is suggested that VEGF-receptor antagonists exhibit anti-tumor effects on various solid tumors.

(4) Ischemia-reperfusion-injury Related Cerebral Edema and Damage

It is believed that VEGF is involved in the etiology of edema due to vascular hyperpermeability effects thereof, and it is reported that in a cerebral ischemia model in the mouse, cerebral edema and damage are inhibited by administration of fused proteins of mouse VEGF-receptor protein (mFlt(1–3)) and IgG (*J. Clin. Invest.*, vol. 104, pp. 1613–1620, 1999).

When the compounds of the present invention are employed as VEGF-receptor antagonists or therapeutic agents for the diseases in which VEGF is involved, they can be administered orally or parenterally.

The dosage forms of the same are tablets, capsules, granules, abstracts, powders, troches, ointments, creams, emulsions, suspensions, suppositories, injections, or the like, each of which may be produced according to the conventional formulation methods (for example, methods defined in the 12th revised edition of the Japanese Pharmacopeia). These dosage forms may be appropriately selected depending on the conditions and ages of the patients, as well as the purpose of the treatment. Upon manufacturing preparations in various formulations, conventional excipients (for example, crystalline cellulose, starch, lactose, mannitol, or the like), binders (for example, hydroxypropylcellulose, polyvinylpyrrolidone, or the like), lubricants (for example, magnesium stearate, talc, or the like), disintegrants (for example, carboxymethylcellulose calcium, or the like), and the like, may be employed.

The doses of the compounds according to the present invention are in the range of 1 to 2000 mg per day in a single dose or divided into several doses, in the case of an adult human subject to be treated. The doses may vary appropriately depending on the age, weight, and condition of each individual patient.

EXAMPLES

Example 1

To a solution of 35.5 g of methyl 4-hydroxybenzoate and 50.2 g of methyl 2-chloro-5-nitrobenzoate dissolved in 500 ml of N,N-dimethylformamide (DMF), was added 48.4 g of anhydrous potassium carbonate, and the mixture was stirred for 3 hours at 80° C. Water was added to the reaction mixture and the whole was extracted with ethyl acetate. The organic layer was washed with saturated brine, and was dried over anhydrous magnesium sulfate. The solvent was removed under reduced pressure. The obtained crude product was recrystallized from methanol to yield 67.7 g of methyl 2-(4-methoxycarbonylphenoxy)-5-nitrobenzoate (melting point: 103–105° C.) (Reaction Scheme (24) described below).

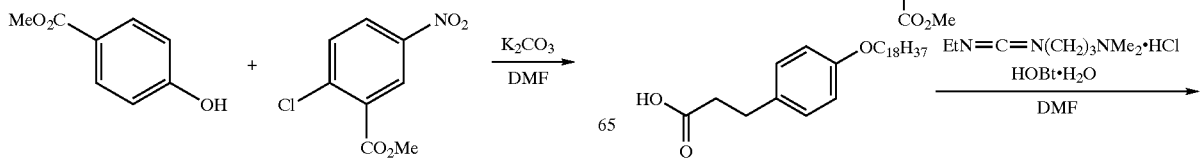

(24)

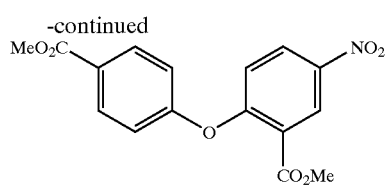

To a suspended mixture of 11.6 g of the compound obtained in the Reaction Scheme (24) described above in 300 ml of methanol, was added 1.00 g of 10% palladium/carbon. Under a hydrogen atmosphere, the mixture was stirred for 2 hours at room temperature. The reaction mixture was filtered to remove the catalyst, and subsequently, the filtrate was concentrated under reduced pressure to yield a crude product. This crude product was purified by silica gel column chromatography (eluent: hexane—ethyl acetate= 2:3), followed by recrystallization from methanol, to yield 8.53 g of methyl 2-(4-methoxycarbonylphenoxy)-5-aminobenzoate (melting point: 144–146° C.) (Reaction Scheme (25) described below).

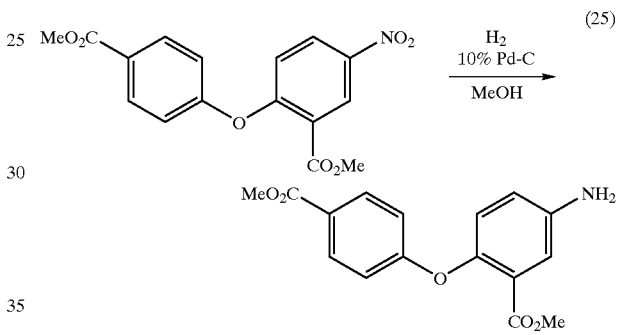

(25)

To a mixture of 3.88 g of the compound obtained in the Reaction Scheme (25) described above, 5.40 g of 3-(4-octadecyloxyphenyl)propionic acid, 2.37 g of 1-hydroxybenzotriazole hydrate (HOBt·H$_2$O), and 4.95 g of 1-(3-(dimethylamino)propyl)-3-ethylcarbodiimide hydrochloride, was added 150 ml of N,N-dimethylformamide. The mixture was stirred for 7 hours at 80° C. Water was added to the reaction mixture and the whole was extracted with ethyl acetate. The organic layer was washed with saturated brine, and was dried over anhydrous magnesium sulfate. The crude product obtained by removal of the solvent under reduced pressure was purified by silica gel column chromatography (eluent: hexane—ethyl acetate=2:1), followed by recrystallization from methanol, to yield 5.02 g of Compound 1 (melting point: 93–95° C.) (Reaction Scheme (26) described below).

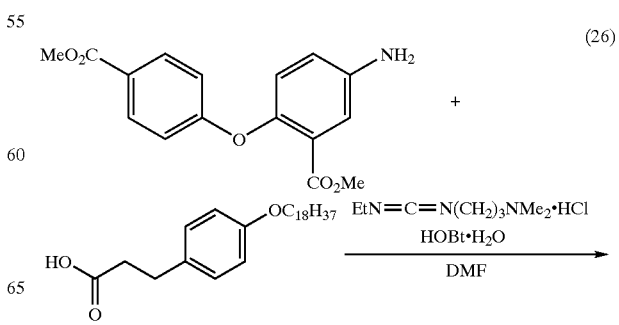

(26)

-continued

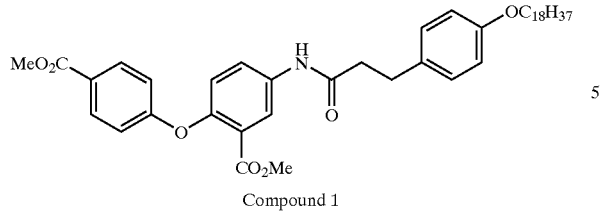

Compound 1

Example 2

To a solution of 35.3 g of methyl 3-hydroxybenzoate and 50.0 g of methyl 2-chloro-5-nitrobenzoate, dissolved in 400 ml of N,N-dimethylformamide, was added 48.1 g of anhydrous potassium carbonate. The mixture was stirred for 3 hours at 80° C. Water was added to the reaction mixture and the whole was extracted with ethyl acetate. The organic layer was washed with saturated brine, and was dried over anhydrous magnesium sulfate. The crude product obtained by removal of the solvent under reduced pressure was purified by recrystallization from methanol to yield 75.4 g of methyl 2-(3-methoxycarbonylphenoxy)-5-nitrobenzoate (melting point: 97–99° C.) (Reaction Scheme (27) described below).

To a suspended mixture of 75.1 g of the compound obtained in the Reaction Scheme (27) described above in 1500 ml of methanol, was added 6.53 g of 10% palladium/carbon. Under a hydrogen atmosphere, the mixture was stirred for 6 hours at room temperature. The reaction mixture was filtered to remove the catalyst, and subsequently, the filtrate was concentrated under reduced pressure to yield a crude product. This crude product was purified by silica gel column chromatography (eluent: chloroform—ethyl acetate=20:1) to yield 68.1 g of methyl 5-amino-2-(3-methoxycarbonylphenoxy)benzoate (yellow viscous substance) (Reaction Scheme (28) described below).

-continued

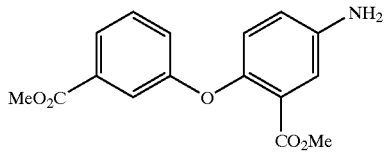

To a mixture of 2.09 g of the compound obtained in the Reaction Scheme (28) described above, 2.90 g of 3-(4-octadecyloxyphenyl)propionic acid, 1.06 g of 1-hydroxybenzotriazole hydrate, and 2.01 g of 1-(3-(dimethylamino)propyl)-3-ethylcarbodiimide hydrochloride, was added 25 ml of N,N-dimethylformamide. The mixture was stirred for one hour at 80° C. Water was added to the reaction mixture and the whole was extracted with ethyl acetate. The organic layer was washed with saturated brine, and was dried over anhydrous magnesium sulfate. The crude product obtained by removal of the solvent under reduced pressure was purified by silica gel column chromatography (eluent:chloroform—ethyl acetate=20:1), followed by recrystallization from methanol to yield 3.45 g of Compound 2 (melting point: 90–92° C.) (Reaction Scheme (29) described below).

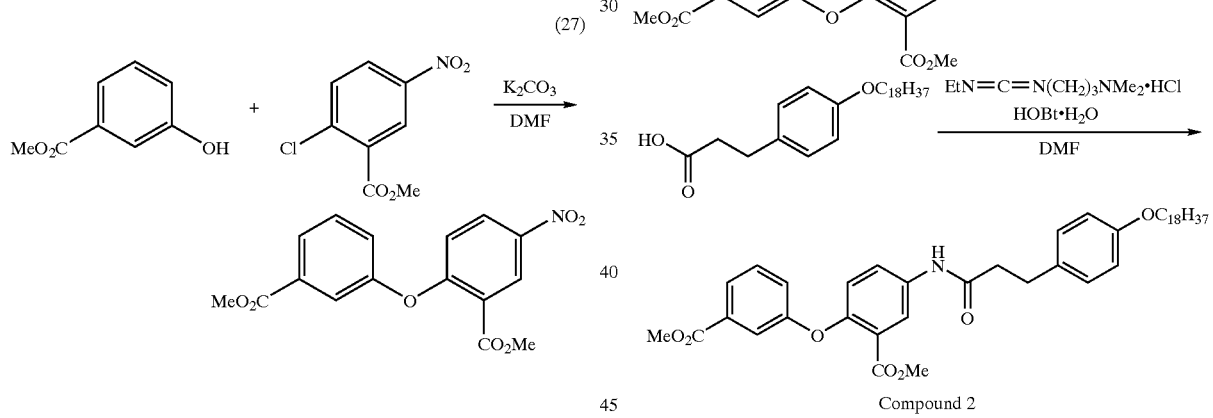

Compound 2

Example 3

Compound 3 to Compound 14 represented by General Formula (30) in which $R^{31}$ to $R^{33}$, n, and X have the structures shown in Table 1 or Table 2, were prepared, in the same procedures as described in Example 1 and Example 2. The melting points of these compounds are also shown in Table 1 and Table 2.

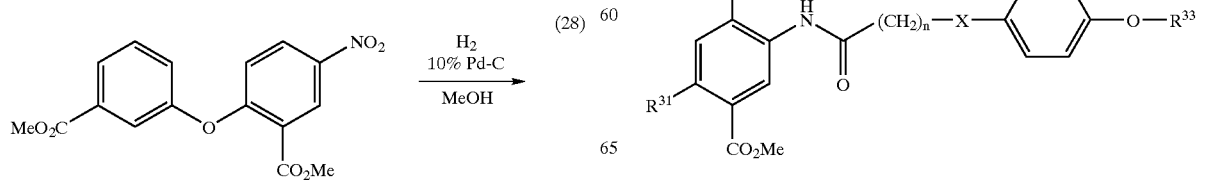

TABLE 1
| | $R^{31}$ | $R^{32}$ | n | X | $R^{33}$ | Melting point (° C.) |
|---|---|---|---|---|---|---|
| Compound 3 | 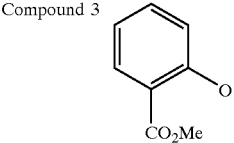 | H | 2 | — | $C_{18}H_{37}$ | 51–53 |
| Compound 4 | 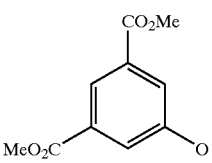 | H | 2 | — | $C_{18}H_{37}$ | 144.5–146 |
| Compound 5 | 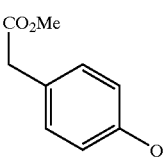 | H | 2 | — | $C_{18}H_{37}$ | 71–73 |
| Compound 6 | 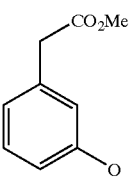 | H | 2 | — | $C_{18}H_{37}$ | 106–110 |
| Compound 7 | 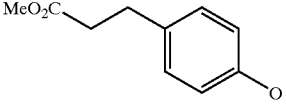 | H | 2 | — | $C_{18}H_{37}$ | 96–98 |
| Compound 8 | 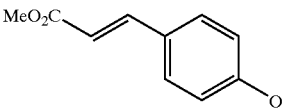 | H | 2 | — | $C_{18}H_{37}$ | 111–113 |
X = "—" means a single bond.
TABLE 2
| | $R^{31}$ | $R^{32}$ | n | X | $R^{33}$ | Melting point (° C.) |
|---|---|---|---|---|---|---|
| Compound 9 | 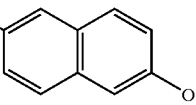 | H | 2 | — | $C_{18}H_{37}$ | 116–118 |
| Compound 10 | H | 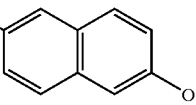 | 2 | — | $C_{18}H_{37}$ | 96–98 |
| Compound 11 | H | 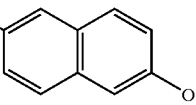 | 2 | — | $C_{18}H_{37}$ | 90.5–91.5 |

TABLE 2-continued

| | $R^{31}$ | $R^{32}$ | n | X | $R^{33}$ | Melting point (° C.) |
|---|---|---|---|---|---|---|
| Compound 12 | H | MeO₂C—[naphthyl]—O— | 2 | — | $C_{18}H_{37}$ | 101–104 |
| Compound 13 | MeO₂C—[phenyl]—O— | H | 1 | — | $C_{18}H_{37}$ | 114–115 |
| Compound 14 | MeO₂C—[phenyl]—O— | H | 3 | O | $C_{16}H_{33}$ | 94–96 |

X = "—" means a single bond.

Example 4

To a mixture of 1.09 g of methyl 2-(4-methoxycarbonylphenylthio)-5-nitrobenzoate obtained in the same procedures as described in Reaction Scheme (24) of Example 1 and 1.75 g of iron powder, were added 3 ml of isopropyl alcohol and an aqueous solution of ammonium chloride (0.05 g of ammonium chloride and 0.95 ml of water). The mixture was stirred for 10 minutes at 85° C. Chloroform was added to the reaction mixture. The mixture was filtered with celite, and was subsequently washed with chloroform. A mixture of the filtrate and the washing was washed with saturated brine, and was subsequently dried over anhydrous magnesium sulfate. After the solvent was removed under reduced pressure, 0.996 g of methyl 5-amino-2-(4-methoxycarbonylphenylthio)benzoate (yellow viscous substance) was obtained (Reaction Scheme (31) described below).

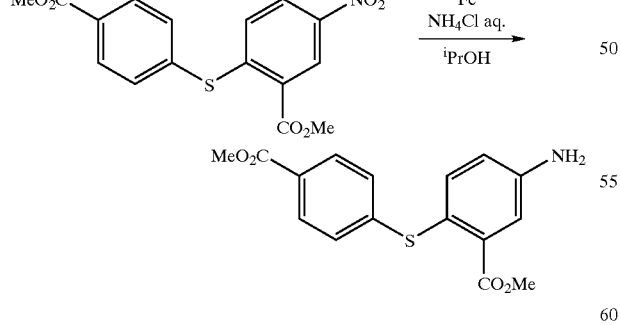

(31)

In the same procedures as described in Reaction Scheme (26) of Example 1, from the compound obtained according to Reaction Scheme (31) described above, Compound 15 (melting point: 115–117° C.) was obtained (Reaction Scheme (32) described below).

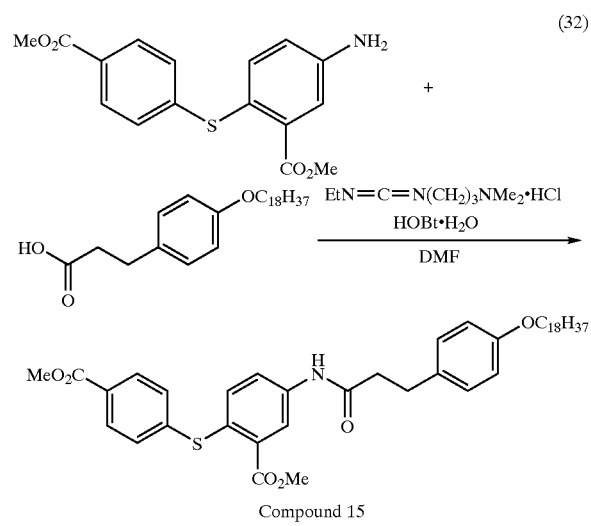

(32)

Example 5

In the same procedures as described in Example 4, Compound 16 to Compound 18 represented by General Formula (33), in which $R^{34}$ and $R^{35}$ have the structures shown in Table 3, were prepared. The melting points of these compounds are also shown in Table 3.

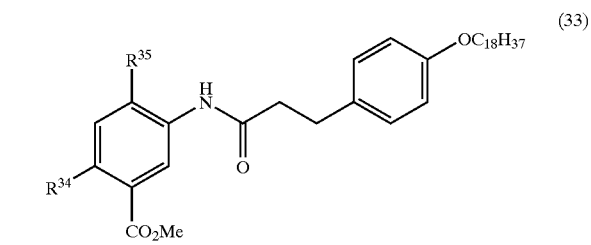

(33)

TABLE 3

| | $R^{34}$ | $R^{35}$ | Melting point (° C.) |
|---|---|---|---|
| Compound 16 | MeO₂C-C₆H₄-S- | H | 89–91 |
| Compound 17 | H | MeO₂C-C₆H₄-S- | 117–119 |
| Compound 18 | MeO₂C-pyridyl-S- | H | 105–107 |

Example 6

To a solution of 11.4 g of 4-aminobenzoic acid and 15.4 g of 2-fluoro-5-nitorobenzoic acid dissolved in 500 ml of N,N-dimethylformamide, were added 22.9 g of anhydrous potassium carbonate and 0.462 g of copper powder. The mixture was stirred for one hour at 100° C., for 3 hours at 120° C., and for 8 hours at 140° C. Water and hydrochloric acid were added thereto so that the reaction mixture was acidified. The precipitated solids were collected by filtration, to yield 120.6 g of a crude product.

To a solution of 20.6 g of the crude product described above dissolved in 500 ml of N,N-dimethylformamide, were added 14.1 g of anhydrous potassium carbonate and 19.3 g of methyl iodide. The mixture was stirred for 2 hours at room temperature. Water was added to the reaction mixture and the whole was extracted with ethyl acetate. The organic layer was washed with saturated brine, and was dried over anhydrous magnesium sulfate. The crude product obtained by removal of the solvent under reduced pressure was suspended in ethyl acetate, followed by filtration, to yield 13.5 g of dimethyl 5-nitro-2,4'-iminodibenzoate (melting point: 205–206° C.) (Reaction Scheme (34) described below)

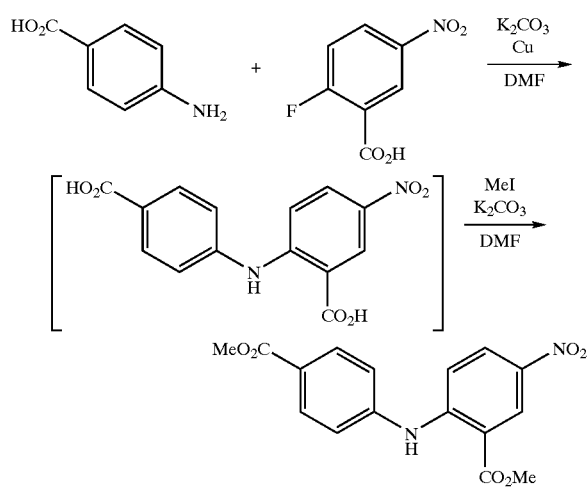

(34)

In the same procedures as described in Reaction Scheme (25) and Reaction Scheme (26) of Example 1, Compound 19 (melting point: 128–130° C.) (Reaction Scheme (35) described below) was prepared from the compound obtained in Reaction Scheme (34) described above.

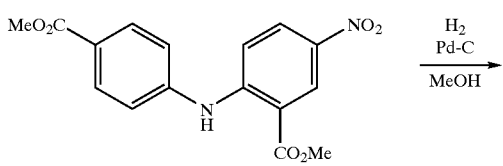

(35)

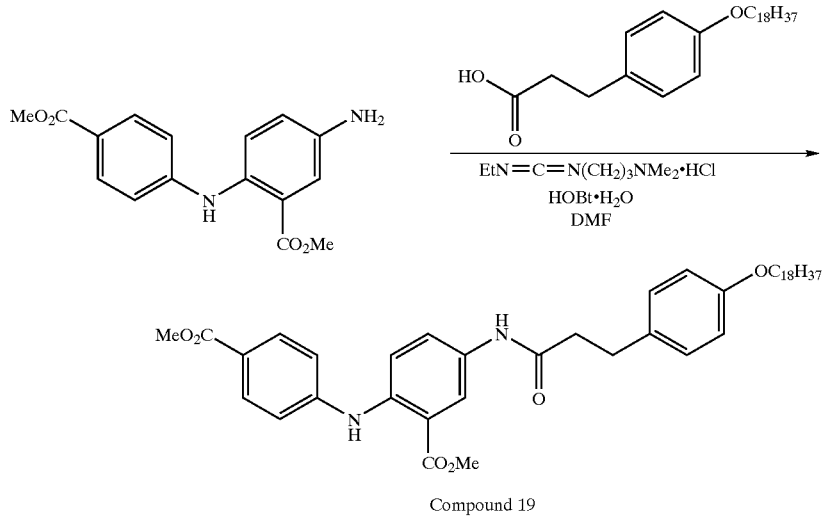

Compound 19

Example 7

In the same procedures as described in Example 6, Compound 20 and Compound 21 represented by General Formula (36), in which $R^{36}$ has the structures shown in Table 4, were prepared. The melting points of these compounds are also shown in Table 4.

(36)

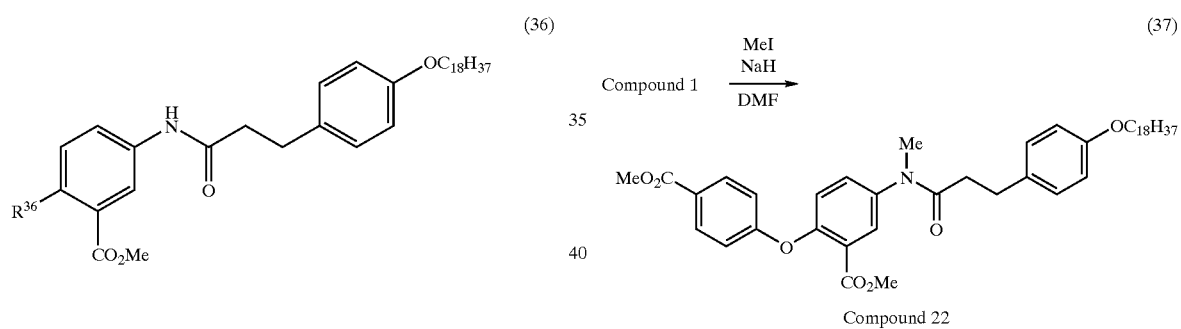

TABLE 4

| | $R^{36}$ | Melting point (° C.) |
|---|---|---|
| Compound 20 | ![structure with MeO2C and NH meta] | 115–117 |
| Compound 21 | ![structure with CO2Me and NH ortho] | 119–121 |

Example 8

To a solution of 524 mg of Compound 1 in 20 ml of N,N-dimethylformamide, were added 45 mg of sodium hydride in oil (60%) and 211 mg of methyl iodide successively. The mixture was stirred for 90 minutes at room temperature. Water was added to the reaction mixture and the whole was extracted with ethyl acetate. The organic layer was washed with saturated brine, and was dried over anhydrous magnesium sulfate. The crude product obtained by removal of the solvent under reduced pressure was purified by silica gel column chromatography (eluent: hexane—ethyl acetate=3:2), followed by recrystallization from methanol, to yield 330 mg of Compound 22 (melting point: 60–62° C.) (Reaction Scheme (37) described below).

(37)

Compound 1 →[MeI, NaH, DMF]

Compound 22

Example 9

In the same procedures as described in Example 8, Compound 23 to Compound 26 represented by General Formula (38), in which $R^{37}$ to $R^{39}$, n, and X have the structures shown in Table 5, were prepared using Compound 3, Compound 10, Compound 14, and Compound 19. The melting points of these compounds are also shown in Table 5.

(38)

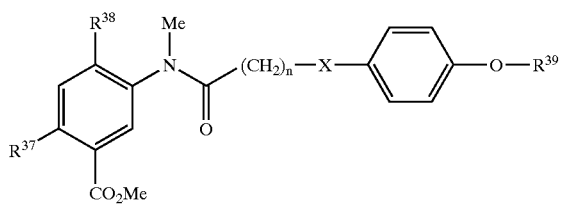

TABLE 5

| | $R^{37}$ | $R^{38}$ | n | X | $R^{39}$ | Melting point (° C.) |
|---|---|---|---|---|---|---|
| Compound 23 | (2-CO₂Me-phenyl-O-) | H | 2 | — | $C_{18}H_{37}$ | 33–34 |
| Compound 24 | H | (3-MeO₂C-phenyl-O-) | 2 | — | $C_{18}H_{37}$ | 77–79 |
| Compound 25 | (4-MeO₂C-phenyl-O-) | H | 3 | O | $C_{16}H_{33}$ | 78–80 |
| Compound 26 | (4-MeO₂C-phenyl-N(Me)-) | H | 2 | — | $C_{18}H_{37}$ | 73–75 |

X = "—" means a single bond.

Example 10

To a suspended mixture of 4.17 g of Compound 1 in 40 ml of ethanol, was added an aqueous solution of sodium hydroxide (2.38 g of sodium hydroxide and 40 ml of water). The mixture was stirred for 3.5 hours at 80° C. To the reaction mixture, 5% hydrochloric acid was added so that the mixture was acidified. The precipitated solids were collected by filtration, and were subsequently washed with water. The obtained solids were dried under reduced pressure at 50 to 70° C., to yield 3.64 g of Compound 27 (melting point: 213–215° C.) (Reaction Scheme (39) described below).

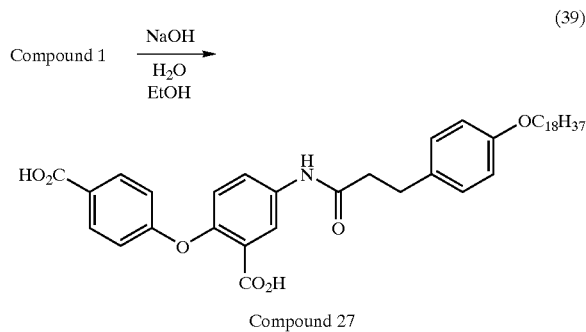

(39)

Compound 1 → (NaOH, H₂O, EtOH) → Compound 27

As a result of differential thermal analysis of Compound 27 obtained herein, an endothermic peak without any fusion was observed at 95° C., an endothermic peak without any fusion was observed at 170° C., and an endothermic peak with fusion was observed at 210° C. The powders of Compound 27 obtained in the Example described above had different patterns of X-ray diffraction at 25° C., 120° C., and 185° C., and for this reason, it was confirmed that Compound 27 had three polymorphic forms.

Example 11

To a mixture of 6.40 g of Compound 2 suspended in 60 ml of tetrahydrofuran (THF) and 60 ml of ethanol, was added an aqueous solution of sodium hydroxide (3.69 g of sodium hydroxide and 60 ml of water). The mixture was stirred for 1.5 hours at 60° C. To the reaction mixture, 10% hydrochloric acid was added so that the mixture was acidified. The precipitated solids were collected by filtration, and were subsequently washed with water. The obtained solids were dried under reduced pressure, to yield 6.00 g of Compound 28 (melting point: 201–205° C.) (Reaction Scheme (40) described below).

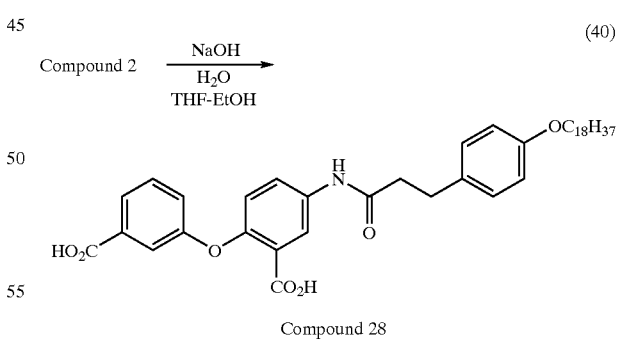

(40)

Compound 2 → (NaOH, H₂O, THF-EtOH) → Compound 28

Example 12

In the same procedures as described in Example 10 and Example 11, Compound 29 to Compound 52 represented by General Formula (41), in which $R^{40}$ to $R^{43}$, n, and X have the structures shown in Table 6 to Table 8, were prepared using Compound 3 to Compound 26. The melting points of these compounds are also shown in Table 6 to Table 8.

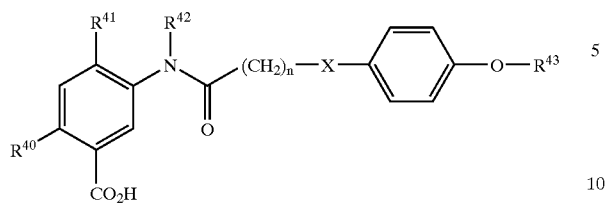
(41)
TABLE 6
| | $R^{40}$ | $R^{41}$ | $R^{42}$ | n | X | $R^{43}$ | Melting point (° C.) |
|---|---|---|---|---|---|---|---|
| Compound 29 | 2-HO₂C-C₆H₄-O- | H | H | 2 | — | $C_{18}H_{37}$ | 184–186 |
| Compound 30 | 3,5-(HO₂C)₂-C₆H₃-O- | H | H | 2 | — | $C_{18}H_{37}$ | 248–254 |
| Compound 31 | 4-(HO₂C-CH₂)-C₆H₄-O- | H | H | 2 | — | $C_{18}H_{37}$ | 170–173 |
| Compound 32 | 3-(HO₂C-CH₂)-C₆H₄-O- | H | H | 2 | — | $C_{18}H_{37}$ | 163–167 |
| Compound 33 | 4-(HO₂C-CH₂CH₂)-C₆H₄-O- | H | H | 2 | — | $C_{18}H_{37}$ | 156–160 |
| Compound 34 | 4-(HO₂C-CH=CH)-C₆H₄-O- | H | H | 2 | — | $C_{18}H_{37}$ | 200–208 |
| Compound 35 | 6-(HO₂C)-naphthyl-2-O- | H | H | 2 | — | $C_{18}H_{37}$ | 215–225 |
| Compound 36 | H | | 3-(HO₂C)-C₆H₄-O- | 2 | — | $C_{18}H_{37}$ | 212–216 |
X = "—" means a single bond.

TABLE 7

| | $R^{40}$ | $R^{41}$ | $R^{42}$ | n | X | $R^{43}$ | Melting point (° C.) |
|---|---|---|---|---|---|---|---|
| Compound 37 | H | 3,5-bis(HO₂C)-phenoxy | H | 2 | — | $C_{18}H_{37}$ | 289–291 |
| Compound 38 | H | 6-(HO₂C)-naphthalen-2-yloxy | H | 2 | — | $C_{18}H_{37}$ | 214–219 |
| Compound 39 | 4-(HO₂C)-phenoxy | H | H | 1 | — | $C_{18}H_{37}$ | 212–217 |
| Compound 40 | 4-(HO₂C)-phenoxy | H | H | 3 | O | $C_{16}H_{33}$ | 200–205 |
| Compound 41 | 4-(HO₂C)-phenylthio | H | H | 2 | — | $C_{18}H_{37}$ | 198–203 |
| Compound 42 | 3-(HO₂C)-phenylthio | H | H | 2 | — | $C_{18}H_{37}$ | 194–198 |
| Compound 43 | H | 3-(HO₂C)-phenylthio | H | 2 | — | $C_{18}H_{37}$ | 246–248 |
| Compound 44 | 5-(HO₂C)-pyridin-2-ylthio | H | H | 2 | — | $C_{18}H_{37}$ | 221–223 |

X = "—" means a single bond.

TABLE 8

| | $R^{40}$ | $R^{41}$ | $R^{42}$ | n | X | $R^{43}$ | Melting point (° C.) |
|---|---|---|---|---|---|---|---|
| Compound 45 | 4-(HO₂C)-phenylamino | H | H | 2 | — | $C_{18}H_{37}$ | 230–235 |
| Compound 46 | 3-(HO₂C)-phenylamino | H | H | 2 | — | $C_{18}H_{37}$ | 235–240 |

TABLE 8-continued

| | $R^{40}$ | $R^{41}$ | $R^{42}$ | n | X | $R^{43}$ | Melting point (° C.) |
|---|---|---|---|---|---|---|---|
| Compound 47 | 2-carboxyanilino (CO$_2$H ortho to NH) | H | H | 2 | — | $C_{18}H_{37}$ | 247–252 |
| Compound 48 | 4-(HO$_2$C)phenoxy | H | Me | 2 | — | $C_{18}H_{37}$ | 96–99 |
| Compound 49 | 2-(CO$_2$H)phenoxy | H | Me | 2 | — | $C_{18}H_{37}$ | 56–61 |
| Compound 50 | H | 3-(HO$_2$C)phenoxy | Me | 2 | — | $C_{18}H_{37}$ | 125–130 |
| Compound 51 | 4-(HO$_2$C)phenoxy | H | Me | 3 | O | $C_{16}H_{33}$ | 127–129 |
| Compound 52 | 4-(HO$_2$C)phenyl-N(Me)- | H | Me | 2 | — | $C_{18}H_{37}$ | 172–177 |

X = "—" means a single bond.

Example 13

To a solution of 10.02 g of methyl 2-chloro-5-nitrobenzoate dissolved in 100 ml of N,N-dimethylformamide, was added 23.92 g of a 15% aqueous solution of sodium methylmercaptan dropwise under ice cooling. The mixture was stirred for 30 minutes. Water was added to the reaction mixture and the whole was extracted with ethyl acetate. The organic layer was washed with saturated brine, and was dried over anhydrous magnesium sulfate. The crude product obtained by removal of the solvent under reduced pressure was recrystallized from ethyl acetate—hexane, to yield 8.76 g of methyl 2-methylthio-5-nitrobenzoate (melting point: 126.5–127.5° C.) (Reaction Scheme (42) described below).

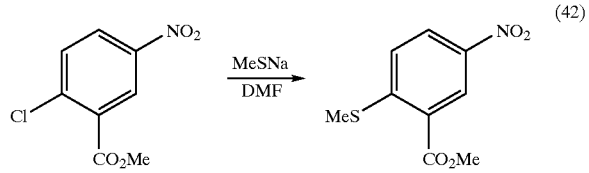

(42)

To a mixture of 8.71 g of the compound obtained in Reaction Scheme (42) described above and 21.41 g of iron powder, were added 20 ml of isopropyl alcohol and an aqueous solution of ammonium chloride (0.62 g of ammonium chloride and 11.5 ml of water). The mixture was stirred for 10 minutes at 85° C. Chloroform was added to the reaction mixture. The mixture was filtered with celite, and was subsequently washed with chloroform. A mixture of the filtrate and the washing was washed with saturated brine, and was subsequently dried over anhydrous magnesium sulfate. The crude product obtained by removal of the solvent under reduced pressure was recrystallized from ethyl acetate-hexane, to yield 7.38 g of methyl 5-amino-2-methylthiobenzoate (melting point: 96–98° C.) (Reaction Scheme (43) described below).

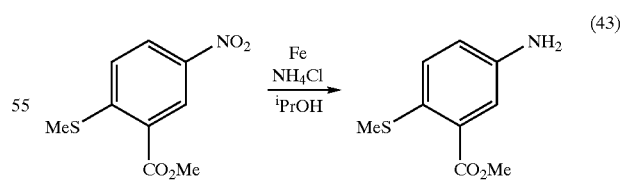

(43)

To a mixture of 2.00 g of the compound obtained in the Reaction Scheme (43) described above, 4.24 g of 3-(4-octadecyloxyphenyl)propionic acid, 2.06 g of 1-hydroxybenzotriazole hydrate, and 3.89 g of 1-(3-(dimethylamino)propyl)-3-ethylcarbodiimide hydrochloride, was added 200 ml of N,N-dimethylformamide. The mixture was stirred for 7 hours at 80° C. Water was added to the reaction mixture and the whole was extracted with ethyl acetate. The organic layer was washed successively with water and saturated brine, and was dried over anhydrous magnesium sulfate. The crude product obtained by removal of the solvent under reduced pressure was recrystallized from methanol, to yield 3.87 g of Compound 53 (melting point: 115–120° C.) (Reaction Scheme (44) described below).

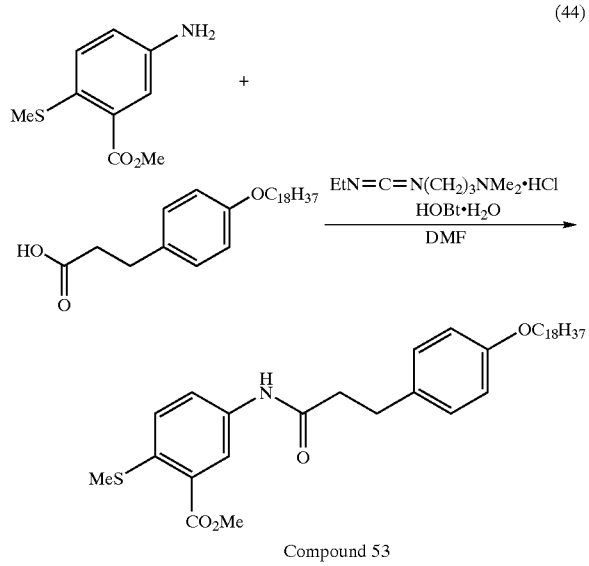

Compound 53

Example 14

To a solution of 1.50 g of the compound obtained in the Reaction Scheme (43) described above and 3.08 g of 4-octadecyloxyphenylacetic acid, dissolved in 70 ml of N,N-dimethylformamide, were added 1.23 g of 1-hydroxybenzotriazole hydrate and 2.92 g of 1-(3-(dimethylamino)propyl)-3-ethylcarbodiimide hydrochloride.

The mixture was stirred for 2.5 hours at 80° C. The reaction mixture was poured into ice-cooled water. The crude product obtained by collection of the precipitated solids by filtration was purified by silica gel column chromatography (eluent: chloroform—ethyl acetate—hexane= 8:1:1), followed by recrystallization from chloroform—methanol, to yield 2.59 g of Compound 54 (melting point: 121–123° C.) (Reaction Scheme (45) described below).

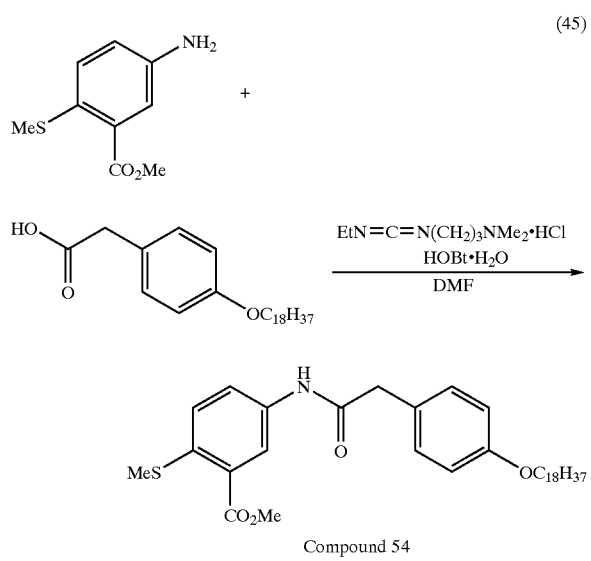

Compound 54

Example 15

In the same procedures as described in Example 13, Compound 55 to Compound 89 represented by General Formula (46), in which $R^{44}$ to $R^{48}$, n, and X have the structures shown in Table 9 to Table 11, were prepared. The melting points of these compounds are also shown in Table 9 to Table 11.

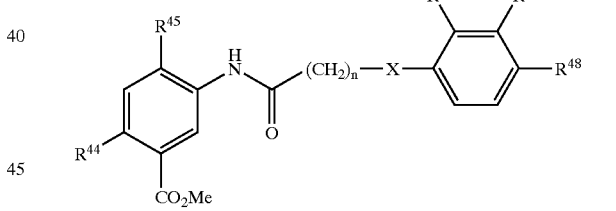

TABLE 9

|  | $R^{44}$ | $R^{45}$ | n | X | $R^{46}$ | $R^{47}$ | $R^{48}$ | Melting point (° C.) |
| --- | --- | --- | --- | --- | --- | --- | --- | --- |
| Compound 55 | MeS | H | 2 | — | H | H | $OC_{20}H_{41}$ | 112–114 |
| Compound 56 | MeS | H | 2 | — | H | H | $OC_{22}H_{45}$ | 115–117 |
| Compound 57 | MeS | H | 2 | — | H | OMe | $OC_{18}H_{37}$ | 113–115 |
| Compound 58 | MeS | H | 2 | — | H | H | $NHCOC_{17}H_{35}$ | 162–166 |
| Compound 59 | MeS | H | 2 | — | H | H | $O(CH_2)_3CO_2Me$ | 132–136 |
| Compound 60 | MeS | H | 2 | — | H | H | $O(CH_2)_5CO_2Et$ | 110–113 |
| Compound 61 | MeS | H | 2 | — | H | H | $O(CH_2)_7CO_2Me$ | 112–115 |
| Compound 62 | MeS | H | 2 | — | H | H | $O(CH_2)_9CO_2Me$ | 106–109 |
| Compound 63 | MeS | H | 2 | — | H | H | $O(CH_2)_{11}CO_2Me$ | 108–110 |

TABLE 9-continued

| | $R^{44}$ | $R^{45}$ | n | X | $R^{46}$ | $R^{47}$ | $R^{48}$ | Melting point (° C.) |
|---|---|---|---|---|---|---|---|---|
| Compound 64 | MeS | H | 2 | — | H | H | (structure: O-propyl-C(=O)-NH-CH2-C(=O)-NH-C10H21) | 154–157 |
| Compound 65 | MeS | H | 2 | — | H | H | (structure: O-propyl-C(=O)-NH-CH(CH2CO2tBu)-C(=O)-NH-C10H21) | 138–158 |

X = "—" means a single bond.

TABLE 10

| | $R^{44}$ | $R^{45}$ | n | X | $R^{46}$ | $R^{47}$ | $R^{48}$ | Melting point (° C.) |
|---|---|---|---|---|---|---|---|---|
| Compound 66 | MeS | H | 1 | — | H | H | $OC_{16}H_{33}$ | 114–115 |
| Compound 67 | MeS | H | 1 | — | H | H | $OC_{14}H_{29}$ | 110–112 |
| Compound 68 | MeS | H | 1 | — | H | H | $OC_{12}H_{25}$ | 107–109 |
| Compound 69 | MeS | H | 1 | — | H | H | $NHCOC_{17}H_{35}$ | 162–165 |
| Compound 70 | MeS | H | 1 | — | H | $NHCOC_{17}H_{35}$ | H | 160–163 |
| Compound 71 | MeS | H | 1 | — | $NHCOC_{17}H_{35}$ | H | H | 174–176 |
| Compound 72 | MeS | H | 1 | O | H | H | $OC_{18}H_{37}$ | 88–90 |
| Compound 73 | MeS | H | 3 | O | H | H | $OC_{16}H_{33}$ | 109–111 |
| Compound 74 | MeS | H | 5 | O | H | H | $OC_{14}H_{29}$ | 121–123 |
| Compound 75 | MeS | H | 7 | O | H | H | $OC_{12}H_{25}$ | 110–115 |
| Compound 76 | MeS | H | 9 | O | H | H | $OC_{10}H_{21}$ | 96–97 |
| Compound 77 | MeS | H | 11 | O | H | H | $OC_8H_{17}$ | 102–105 |
| Compound 78 | MeS | H | 3 | O | $CO_2Me$ | H | $OC_{16}H_{33}$ | 105–107 |
| Compound 79 | MeS | H | 5 | O | $CO_2Me$ | H | $OC_{14}H_{29}$ | 83–85 |
| Compound 80 | MeS | H | 7 | O | $CO_2Me$ | H | $OC_{12}H_{25}$ | 83–86 |

X = "—" means a single bond.

TABLE 11

| | $R^{44}$ | $R^{45}$ | n | X | $R^{46}$ | $R^{47}$ | $R^{48}$ | Melting point (° C.) |
|---|---|---|---|---|---|---|---|---|
| Compound 81 | MeS | H | 0 | CH=CH | H | H | $OC_{18}H_{37}$ | 113–115 |
| Compound 82 | EtS | H | 1 | — | H | H | $OC_{18}H_{37}$ | 108–110 |
| Compound 83 | PrS | H | 1 | — | H | H | $OC_{18}H_{37}$ | 100–101.5 |
| Compound 84 | MeO-CH2CH2-O-CH2CH2-S- | H | 1 | — | H | H | $OC_{18}H_{37}$ | 93.5–97.5 |
| Compound 85 | MeO-CH2CH2-O-CH2CH2CH2CH2-SH | H | 1 | — | H | H | $OC_{18}H_{37}$ | 79.5–80.5 |
| Compound 86 | H | MeS | 2 | — | H | H | $OC_{18}H_{37}$ | 103–105 |
| Compound 87 | H | EtS | 2 | — | H | H | $OC_{18}H_{37}$ | 93–97 |
| Compound 88 | H | PrS | 2 | — | H | H | $OC_{18}H_{37}$ | 89–90 |
| Compound 89 | H | $PhCH_2S$ | 2 | — | H | H | $OC_{18}H_{37}$ | 97–99 |

X = "—" means a single bond.

Example 16

To a solution of 1.20 g of Compound 53 dissolved in 50 ml of N,N-dimethylformamide, were added 250 μl of methyl iodide and 120 mg of sodium hydride in oil (60%) under ice cooling. The mixture was stirred for 2 hours at room temperature. In addition, 500 μl of methyl iodide and 120 mg of sodium hydride in oil (60%) were added thereto. The mixture was stirred for 3.5 hours at room temperature. Water was added to the reaction mixture and the whole was extracted with ethyl acetate. The organic layer was washed with saturated brine, and was dried over anhydrous magnesium sulfate. The crude product obtained by removal of the solvent under reduced pressure was purified by silica gel column chromatography (eluent: hexane—ethyl acetate—chloroform=1:1:1) to yield 867 mg of Compound 90 (melting point: 65.5–66.5° C.) (Reaction Scheme (47) described below).

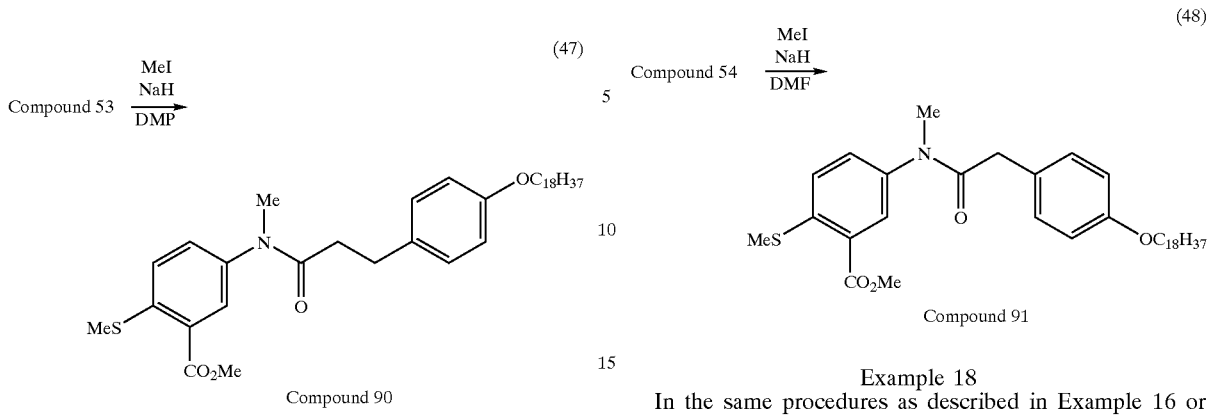

Compound 90

Compound 91

Example 17

To a solution of 6.60 g of Compound 54 dissolved in 150 ml of N,N-dimethylformamide, were added 1.5 ml of methyl iodide and 678 mg of sodium hydride in oil (60%). The mixture was stirred for 2.5 hours at room temperature. Water was added to the reaction mixture and the whole was extracted with ethyl acetate. The organic layer was washed with saturated brine, and was dried over anhydrous magnesium sulfate. The crude product obtained by removal of the solvent under reduced pressure was purified by silica gel column chromatography (eluent: hexane—ethyl acetate= 2:1) to yield 5.29 g of Compound 91 (melting point: 60–69° C.) (Reaction Scheme (48) described below).

Example 18

In the same procedures as described in Example 16 or Example 17, Compound 92 to Compound 95 represented by General Formula (49), in which $R^{49}$ to $R^{51}$, n, and X have the structures shown in Table 12 were prepared using Compound 53 as a starting material and the corresponding reagents. In addition, in the same procedures as described in Example 16 or Example 17, Compound 96 to Compound 101 represented by General Formula (49), in which $R^{49}$ to $R^{51}$, n, and X have the structures shown in Table 12, were prepared using Compound 73, and Compound 81 to Compound 85 as starting materials. The melting points of these compounds are also shown in Table 12.

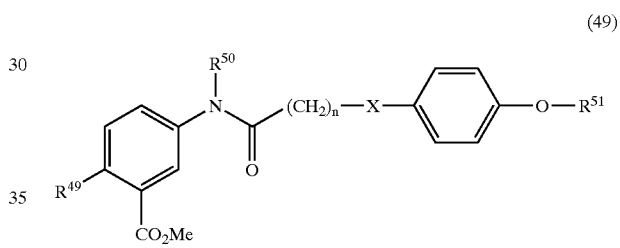

(49)

TABLE 12

| | $R^{49}$ | $R^{50}$ | n | X | $R^{51}$ | Melting point (° C.) |
|---|---|---|---|---|---|---|
| Compound 92 | MeS | Et | 2 | — | $C_{18}H_{37}$ | 48–51 |
| Compound 93 | MeS | $CH_2$—△ | 2 | — | $C_{18}H_{37}$ | 52–53 |
| Compound 94 | MeS | $CH_2Ph$ | 2 | — | $C_{18}H_{37}$ | 80–82 |
| Compound 95 | MeS | $CH_2CO_2{}^tBu$ | 2 | — | $C_{18}H_{37}$ | 55–57 |
| Compound 96 | MeS | Me | 3 | O | $C_{16}H_{33}$ | 79–81 |
| Compound 97 | MeS | Me | 0 | CH=CH | $C_{18}H_{37}$ | 103–106 |
| Compound 98 | EtS | Me | 1 | — | $C_{18}H_{37}$ | 50–51.5 |
| Compound 99 | PrS | Me | 1 | — | $C_{18}H_{37}$ | 57–58 |
| Compound 100 | MeO∼O∼S | Me | 1 | — | $C_{18}H_{37}$ | 70–74.5 |
| Compound 101 | MeO∼O∼∼S | Me | 1 | — | $C_{18}H_{37}$ | 48.5–50.5 |

X = "—" means a single bond.

Example 19

To a solution of 777 mg of Compound 95 dissolved in 5 ml of methylene chloride, was added 5 ml of trifluoroacetic acid. The mixture was stirred for one hour at room temperature. The crude product obtained by removal of the reaction mixture under reduced pressure was purified by silica gel column chromatography (eluent: chloroform—ethyl acetate=3:2), to yield 750 mg of Compound 102 (melting point: 102–106° C.) (Reaction Scheme (50) described below)

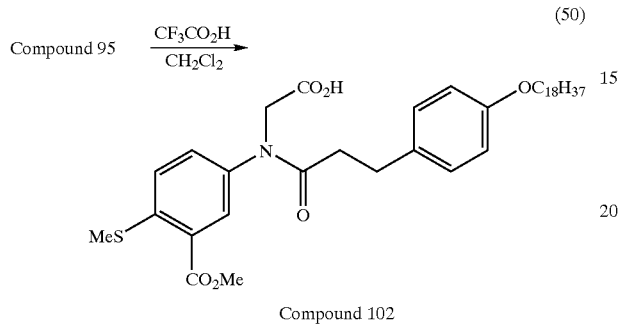

Example 20

To a solution of 200 mg of Compound 102 dissolved in 1.0 ml of N,N-dimethylformamide, were added a solution of 60 mg of methylamine hydrochloride and 50 mg of triethylamine, dissolved in 0.5 ml of N,N-dimethylformamide. Successively, 82 mg of 1-hydroxybenzotriazole hydrate, and 117 mg of 1-(3-(dimethylamino)propyl)-3-ethylcarbodiimide hydrochloride were added. The mixture was stirred for one hour at room temperature. Water was added to the reaction mixture and the whole was extracted with chlorform. The organic layer was dried over anhydrous magnesium sulfate. The crude product obtained by removal of the solvent under reduced pressure was purified by silica gel column chromatography (eluent: chloroform—ethyl acetate=4:1), to yield 135 mg of Compound 103 (melting point: 119–121° C.) (Reaction Scheme (51) described below).

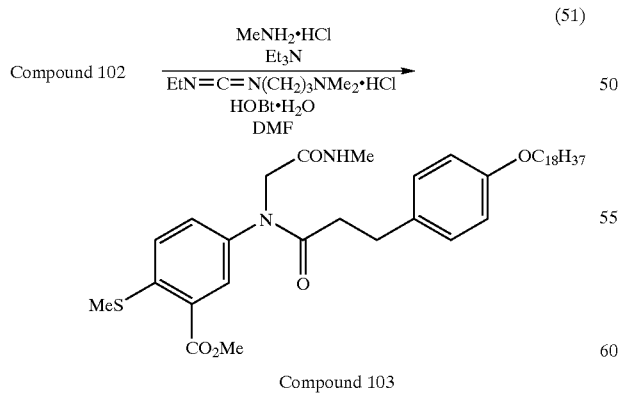

Example 21

To a mixture of 900 mg of Compound 102 dissolved in 25 ml of N,N-dimethylformamide, were added 351 mg of 1,1-di(p-anisyl)methylamine, 278 mg of 1-hydroxybenzotriazole hydrate, and 526 mg of 1-(3-(dimethylamino)propyl)-3-ethylcarbodiimide hydrochloride. The mixture was stirred for 5 hours at 80° C. Ethyl acetate was added to the reaction mixture and the whole was washed successively with water and saturated brine. The organic layer was dried over anhydrous magnesium sulfate. The crude product obtained by removal of the solvent under reduced pressure was purified by silica gel column chromatography (eluent: chloroform—ethyl acetate=3:1) to yield 808 mg of a 1,1-di(p-anisyl)methylamide compound (melting point: 127–129° C.) (Reaction Scheme (52) described below).

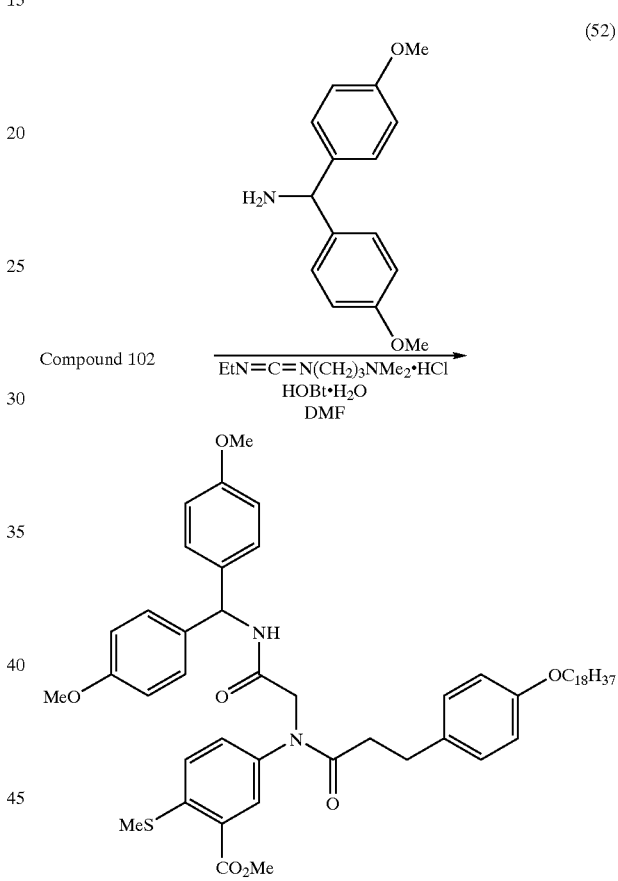

To a solution of 498 mg of the compound obtained in Reaction Scheme (52) dissolved in 10 ml of methylene chloride, were added 1.3 ml of dimethylsulfide and 8 ml of trifluoroacetic acid. The mixture was stirred for 4 hours at room temperature. Ethyl acetate was added to the reaction mixture, and the whole was washed successively with a saturated aqueous solution of sodium hydrogencarbonate and saturated brine. The organic layer was dried over anhydrous magnesium sulfate. The crude product obtained by removal of the solvent under reduced pressure was purified by silica gel column chromatography (eluent: chloroform—ethyl acetate=1:9), to yield 367 mg of Compound 104 (melting point: 113–116° C.) (Reaction Scheme (53) described below).

(53)

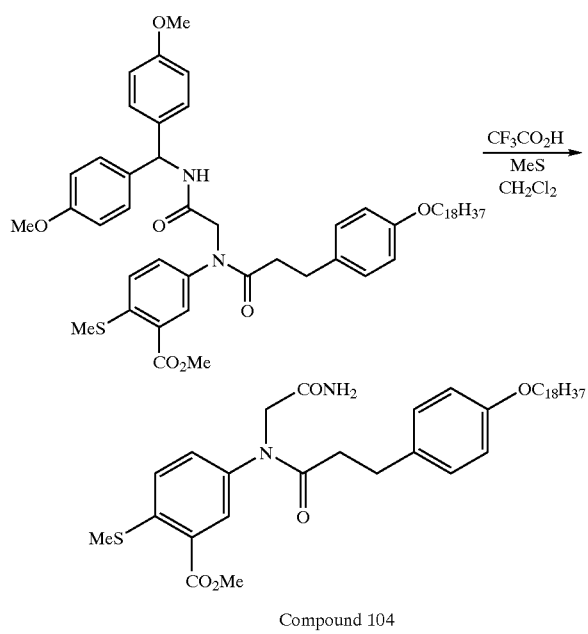

Compound 104

Example 22

To a solution of 383 mg of Compound 65 dissolved in 5 ml of methylene chloride, was added 5 ml of trifluoroacetic acid. The mixture was stirred for 2 hours at room temperature. The crude product obtained by removal of the reaction mixture under reduced pressure was purified by silica gel column chromatography (eluent: chloroform—methanol= 5:1), followed by recrystallization from methanol, to yield 302 mg of Compound 105 (melting point: 165–167° C.) (Reaction Scheme (54) described below).

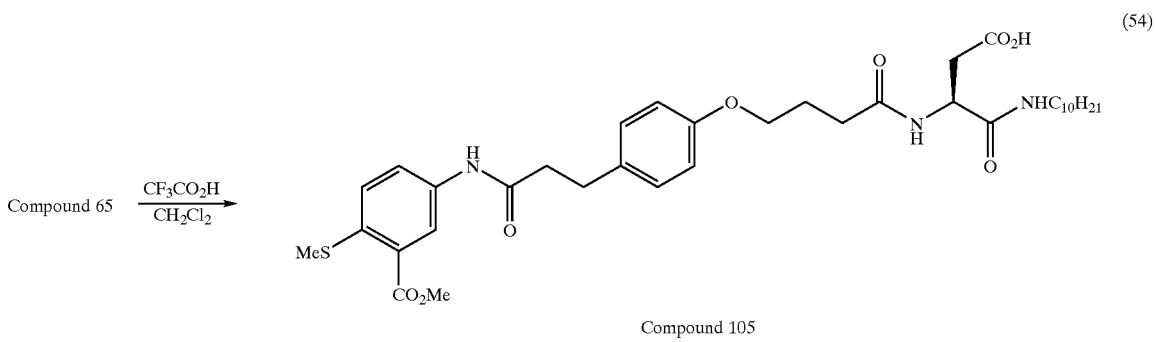

Compound 105

Example 23

To a suspension of 800 mg of Compound 53 suspended in 50 ml of methylene chloride, was added 290 mg of m-chloroperoxybenzoic acid (mCPBA). The mixture was stirred for one hour at room temperature. In addition, 33 mg of m-chloroperoxybenzoic acid were added thereto, and the mixture was stirred for 30 minutes at room temperature. A saturated aqueous solution of sodium hydrogencarbonate was added to the reaction mixture. The whole was extracted with chloroform, and the organic layer was dried over anhydrous magnesium sulfate. The crude product obtained by removal of the solvent under reduced pressure was purified by silica gel column chromatography (eluent: chloroform—ethyl acetate=1:1), to yield 697 mg of Compound 106 (melting point: 65–67° C.) (Reaction Scheme (55) described below).

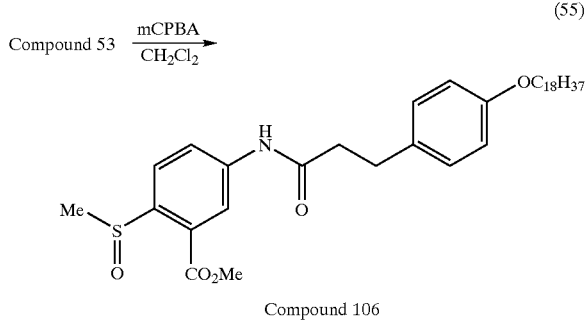

Compound 106

Example 24

Tert-butyl 2-methylthio-5-nitrobenzoate (melting point: 112–113° C.) was prepared using t-butyl 2-chloro-5-nitrobenzoate, in the same procedures as described in Reaction Scheme (42) of Example 13 (Reaction Scheme (56) described below).

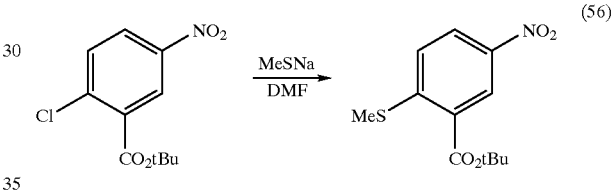

Tert-butyl 5-amino-2-methylthiobenzoate (melting point: 76–78° C.) was prepared using the compound obtained in Reaction Scheme (56) described above in the same procedures as described in Reaction Scheme (43) of Example 13 (Reaction Scheme (57) described below).

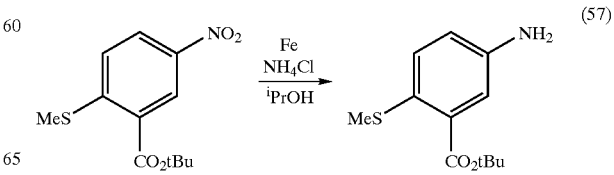

To a solution of 15.0 g of 4-aminophenol dissolved in 300 ml of N,N-dimethylformamide, was added 28.5 g of anhydrous potassium carbonate. Subsequently, 46.0 g of 1-bromooctadecane was added thereto at 80° C., and the mixture was stirred for 3.5 hours at 80° C. Water was added to the reaction mixture, and the whole was extracted with ethyl acetate. The organic layer was washed with saturated brine, and was dried over anhydrous magnesium sulfate. The crude product obtained by removal of the solvent under reduced pressure was purified by silica gel column chromatography (eluent: hexane—ethyl acetate—chloroform=5:1:1 to 1:1:1), followed by recrystallization from chloroform—methanol, to yield 20.28 g of 4-octadecyloxyaniline (melting point: 95–97° C.) (Reaction Scheme (58) described below).

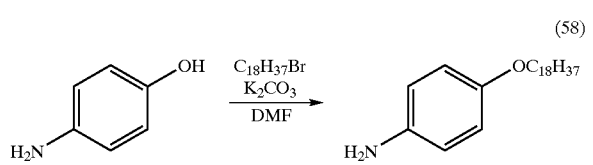
(58)

To a solution of 15.0 g of the compound obtained in Reaction Scheme (58) described above, dissolved in 500 ml of methylene chloride, were added 8.4 g of triethylamine and 11.8 g of di-t-butyl dicarbonate. The mixture was stirred for 15.5 hours at room temperature. After the reaction mixture was washed with saturated brine, the organic layer was dried over anhydrous magnesium sulfate. The crude product obtained by removal of the solvent under reduced pressure was purified by silica gel column chromatography (eluent: hexane—ethyl acetate—chloroform=3:1:1), to yield 12.53 g of N-t-butoxycarbonyl-4-octadecyloxyaniline (melting point: 66–67° C.) (Reaction Scheme (59) described below).

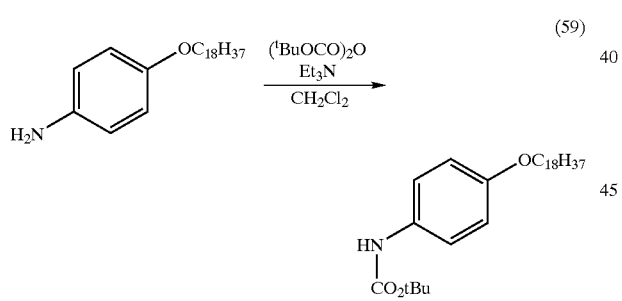
(59)

To a solution of 500 mg of the compound obtained in Reaction Scheme (59) described above, dissolved in 3 ml of N,N-dimethylformamide, was added 70 mg of sodium hydride in oil (60%). The mixture was stirred for 10 minutes at room temperature. Subsequently, 370 mg of ethyl bromoacetate was added thereto, and the mixture was stirred for 30 minutes at room temperature. Water was added to the reaction mixture and the whole was extracted with ethyl acetate. The organic layer was washed with saturated brine, and was dried over anhydrous magnesium sulfate. The crude product obtained by removal of the solvent under reduced pressure was purified by silica gel column chromatography (eluent: hexane—ethyl acetate—chloroform=4:1:1) to yield 471 mg of ethyl N-t-butoxycarbonyl-N-(4-octadecyloxyphenyl)glycine (pale brown viscous substance) (Reaction Scheme (60) described below).

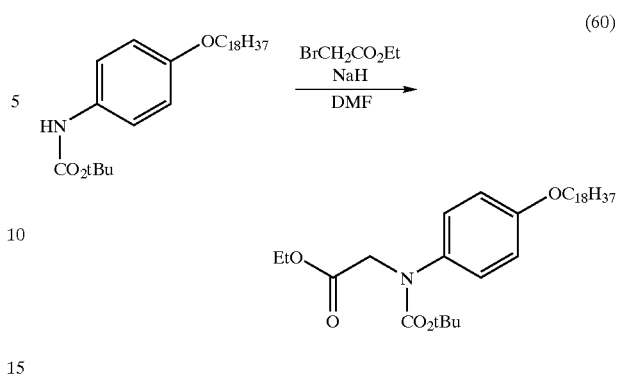
(60)

To a solution of 200 mg of the compound obtained in Reaction Scheme (60) described above, dissolved in 2 ml of tetrahydrofuran and 2 ml of ethanol, was added an aqueous solution of sodium hydroxide (92 mg of sodium hydroxide and 2 ml of water). The mixture was stirred for 30 minutes at room temperature. To the reaction mixture, was added diluted hydrochloric acid under cooling with an ice bath so that the mixture was acidified. The mixture was extracted with chloroform, and the organic layer was dried over anhydrous magnesium sulfate. After the solvent was removed under reduced pressure, 170 mg of N-t-butoxycarbonyl-N-(4-octadecyloxyphenyl)glycine (melting point: 89–92.5° C.) was obtained (Reaction Scheme (61) described below).

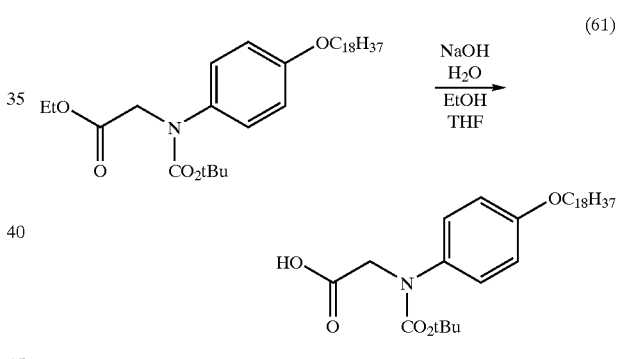
(61)

Compound 107 (pale yellow viscous substance) was prepared using the compound obtained in Reaction Scheme (57) described above and the compound obtained in Reaction Scheme (61) described above, in the same procedures as described in Reaction Scheme (44) of Example 13 or Example 14 (Reaction Scheme (62) described below).

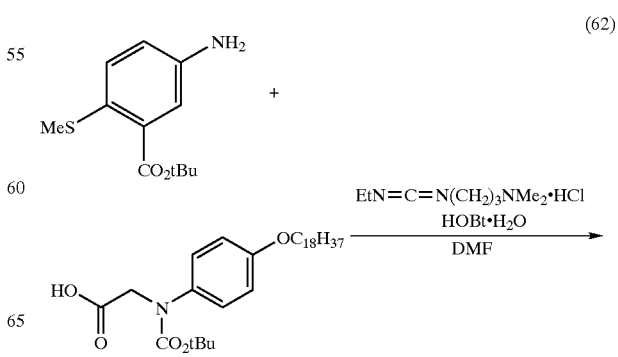
(62)

-continued

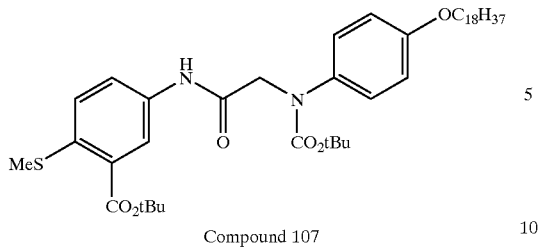

Compound 107

Example 25

Methyl 3-(4-(t-butoxycarbonylamino)phenyl)propionate (melting point: 72–73.5° C.) was prepared using methyl 3-(4-aminophenyl)propionate in the same procedures as described in Reaction Scheme (59) of Example 24 (Reaction Scheme (63) described below).

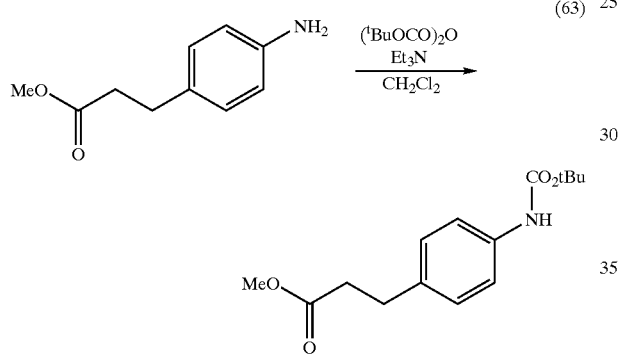

(63)

To a solution of 2.03 g of the compound obtained in Reaction Scheme (63) described above, dissolved in 20 ml of N,N-dimethylformamide, were added 436 mg of sodium hydride in oil (60%) and 2.67 g of 1-bromooctadecane at room temperature. The mixture was stirred for 3.5 hours at 40° C. Water was added to the reaction mixture and the whole was extracted with ethyl acetate. The organic layer was washed with saturated brine, and was dried over anhydrous magnesium sulfate. The crude product obtained by removal of the solvent under reduced pressure was purified by silica gel column chromatography (eluent: hexane—ethyl acetate—chloroform=4:1:1) to yield 1.59 g of methyl 3-(4-(N-octadecyl-t-butoxycarbonylamino)phenyl)propionate (colorless viscous substance) (Reaction Scheme (64) described below).

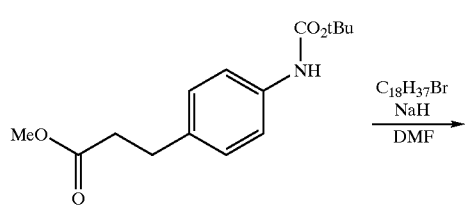

(64)

-continued

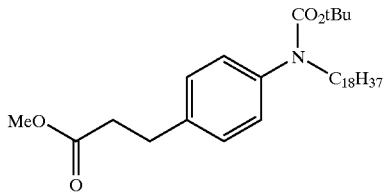

3-(4-(N-octadecyl-t-butoxycarbonylamino)phenyl)-propionic acid (melting point: 46–48° C.) was prepared using the compound obtained in Reaction Scheme (64) described above, in the same procedures as described in Reaction Scheme (61) of Example 24 (Reaction Scheme (65) described below).

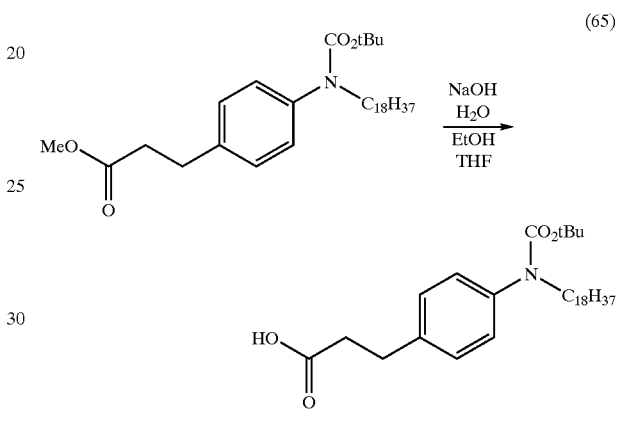

(65)

Compound 108 (pale yellow viscous substance) was prepared using the compound obtained in Reaction Scheme (57) of Example 24 and the compound obtained in Reaction Scheme (65) described above, in the same procedures as described in Reaction Scheme (44) of Example 13 or Example 14 (Reaction Scheme (66) described below).

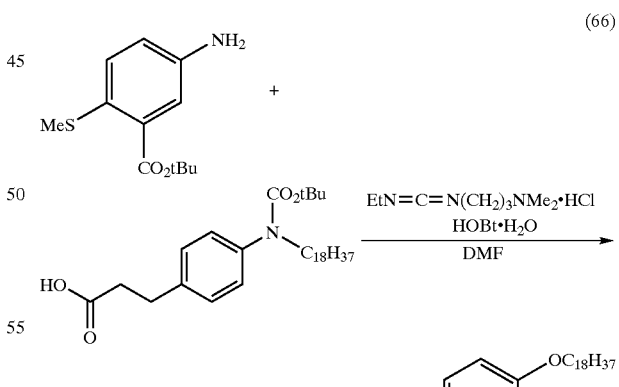

(66)

Compound 108

Example 26

To a solution of 1.69 g of Compound 100 dissolved in 15 ml of tetrahydrofuran and 5 ml of methanol, was added 2 ml of 4M hydrochloric acid. The mixture was stirred for 22.5 hours at 50° C. Water was added to the reaction mixture and the whole was extracted with chloroform. The organic layer was washed with a saturated aqueous solution of sodium hydrogencarbonate, and was dried over anhydrous magnesium sulfate. The crude product obtained by removal of the solvent under reduced pressure was purified by silica gel column chromatography (successive eluents: hexane—ethyl acetate—chloroform=1:2:2 and 1:3:1, and hexane—ethyl acetate=1:4) to yield 1.27 g of Compound 109 (melting point: 92.5–94° C.) (Reaction Scheme (67) described below)

(67)

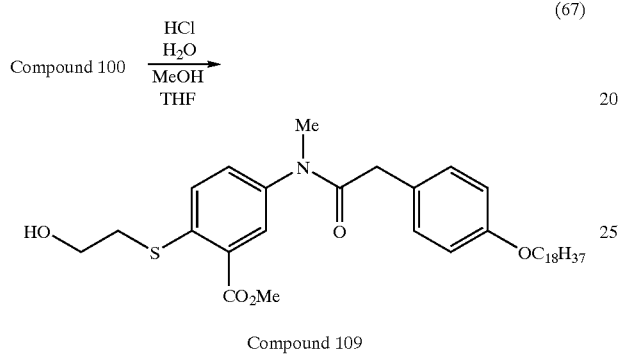

Compound 109

Example 27

Compound 110 to Compound 112 represented by General Formula (68), in which $R^{52}$ and m have the structures shown in Table 13, were prepared using Compound 101, Compound 84, and Compound 85, respectively, in the same procedures as described in Example 26. The melting points of these compounds are also shown in Table 13.

(68)

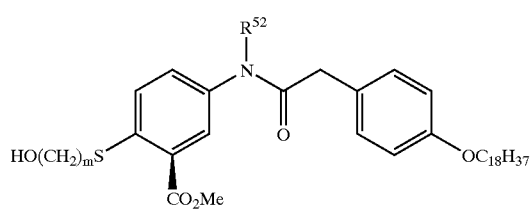

TABLE 13

| | m | $R^{52}$ | Melting point (° C.) |
|---|---|---|---|
| Compound 110 | 3 | Me | 38.5–40 |
| Compound 111 | 2 | H | 66–70 |
| Compound 112 | 3 | H | 101–110 |

Example 28

To a solution of 850 mg of Compound 90 dissolved in 10 ml of tetrahydrofuran and 10 ml of ethanol, was added an aqueous solution of sodium hydroxide (577 mg of sodium hydroxide and 10 ml of water). The mixture was stirred for 45 minutes at 50° C. To the reaction mixture, diluted hydrochloric acid was added so that the mixture was acidified. The precipitated solids were collected by filtration, and subsequently washed successively with water and ethanol. The obtained solids were dried under reduced pressure, to yield 770 mg of Compound 113 (melting point: 106–108° C.) (Reaction Scheme (69) described below).

(69)

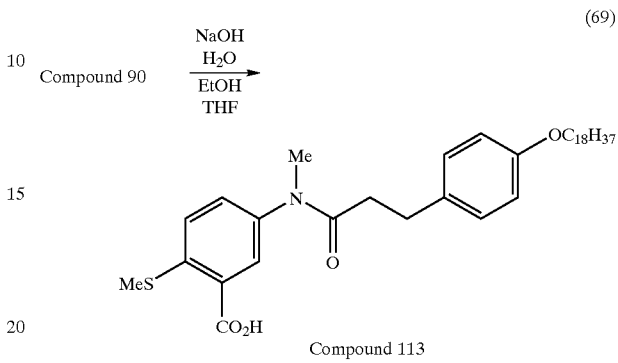

Compound 113

Example 29

1) To a solution of 5.27 g of Compound 91 dissolved in 50 ml of tetrahydrofuran and 50 ml of ethanol, was added an aqueous solution of sodium hydroxide (3.52 g of sodium hydroxide and 50 ml of water). The mixture was stirred for 1.5 hours at 50° C. To the reaction mixture, 10% hydrochloric acid was added so that the mixture was acidified. The precipitated solids were collected by filtration, and were subsequently washed with water. The obtained solids were dried under reduced pressure to yield 4.93 g of Compound 114 (melting point: 104–106° C.).

2) To a solution of 254 mg of Compound 91 dissolved in 3 ml of tetrahydrofuran and 3 ml of ethanol, was added an aqueous solution of sodium hydroxide (190 mg of sodium hydroxide and 3 ml of water). The mixture was stirred for 5 hours at 50° C. To the reaction mixture, diluted hydrochloric acid was added so that the mixture was acidified. The whole was extracted with chloroform, and the organic layer was subsequently dried over anhydrous magnesium sulfate. The crude product obtained by removal of the solvent under reduced pressure was purified by silica gel column chromatography (eluent: chloroform—methanol=20:1) to yield 185 mg of Compound 114 (melting point: 49–51° C.) (Reaction Scheme (70) described below).

(70)

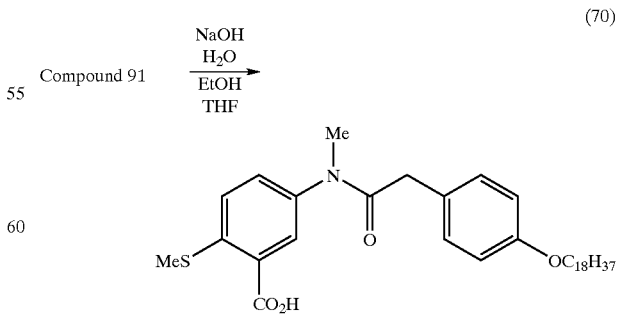

Compound 114

Example 30

Compound 115 to Compound 162 represented by General Formula (71), in which $R^{53}$ to $R^{58}$, n, and X have the structures shown in Table 14 to Table 17, were prepared using Compound 53 to Compound 64, Compound 66 to Compound 83, Compound 86 to Compound 89, Compound 92 to Compound 94, Compound 96 to Compound 99, Compound 102 to Compound 106, and Compound 109 to Compound 110, in the same procedures as described in Example 28 and Example 29. The melting points of these compounds are also shown in Table 14 to Table 17.

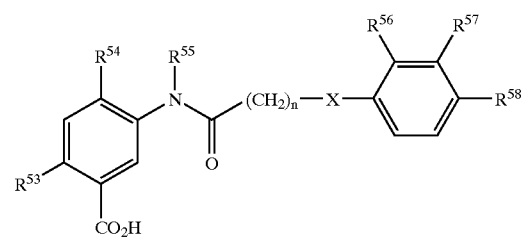

(71)

TABLE 14

| | $R^{53}$ | $R^{54}$ | $R^{55}$ | n | X | $R^{56}$ | $R^{57}$ | $R^{58}$ | Melting point (° C.) |
|---|---|---|---|---|---|---|---|---|---|
| Compound 115 | MeS | H | H | 2 | — | H | H | $OC_{18}H_{37}$ | 185–194 |
| Compound 116 | MeS | H | H | 1 | — | H | H | $OC_{18}H_{37}$ | 200–204 |
| Compound 117 | MeS | H | H | 2 | — | H | H | $OC_{20}H_{41}$ | 211–213 |
| Compound 118 | MeS | H | H | 2 | — | H | H | $OC_{22}H_{45}$ | 209–212 |
| Compound 119 | MeS | H | H | 2 | — | H | OMe | $OC_{18}H_{37}$ | 174–176 |
| Compound 120 | MeS | H | H | 2 | — | H | H | $NHCOC_{17}H_{35}$ | 257–260 |
| Compound 121 | MeS | H | H | 2 | — | H | H | $O(CH_2)_3CO_2H$ | 228–232 |
| Compound 122 | MeS | H | H | 2 | — | H | H | $O(CH_2)_5CO_2H$ | 218–222 |
| Compound 123 | MeS | H | H | 2 | — | H | H | $O(CH_2)_7CO_2H$ | 209–213 |
| Compound 124 | MeS | H | H | 2 | — | H | H | $O(CH_2)_9CO_2H$ | 200–203 |
| Compound 125 | MeS | H | H | 2 | — | H | H | $O(CH_2)_{11}CO_2H$ | 192–195 |
| Compound 126 | MeS | H | H | 2 | — | H | H | 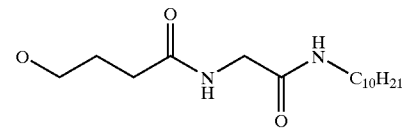 | 130–135 |

X = "—" means a single bond.

TABLE 15

| | $R^{53}$ | $R^{54}$ | $R^{55}$ | n | X | $R^{56}$ | $R^{57}$ | $R^{58}$ | Melting point (° C.) |
|---|---|---|---|---|---|---|---|---|---|
| Compound 127 | MeS | H | H | 1 | — | H | H | $OC_{16}H_{33}$ | 200–205 |
| Compound 128 | MeS | H | H | 1 | — | H | H | $OC_{14}H_{29}$ | 200–204 |
| Compound 129 | MeS | H | H | 1 | — | H | H | $OC_{12}H_{25}$ | 199–203 |
| Compound 130 | MeS | H | H | 1 | — | H | H | $NHCOC_{17}H_{35}$ | 214–217 |
| Compound 131 | MeS | H | H | 1 | — | H | $NHCOC_{17}H_{35}$ | H | 224–228 |
| Compound 132 | MeS | H | H | 1 | — | $NHCOC_{17}H_{35}$ | H | H | 247–250 |
| Compound 133 | MeS | H | H | 1 | O | H | H | $OC_{18}H_{37}$ | 165–169 |
| Compound 134 | MeS | H | H | 3 | O | H | H | $OC_{16}H_{33}$ | 197–202 |
| Compound 135 | MeS | H | H | 5 | O | H | H | $OC_{14}H_{29}$ | 199–202 |
| Compound 136 | MeS | H | H | 7 | O | H | H | $OC_{12}H_{25}$ | 193–196 |
| Compound 137 | MeS | H | H | 9 | O | H | H | $OC_{10}H_{21}$ | 185–188 |
| Compound 138 | MeS | H | H | 11 | O | H | H | $OC_8H_{17}$ | 180–185 |
| Compound 139 | MeS | H | H | 3 | O | $CO_2H$ | H | $OC_{16}H_{33}$ | 168–171 |
| Compound 140 | MeS | H | H | 5 | O | $CO_2H$ | H | $OC_{14}H_{29}$ | 169–174 |
| Compound 141 | MeS | H | H | 7 | O | $CO_{2H}$ | H | $OC_{12}H_{25}$ | 164–168 |
| Compound 142 | MeS | H | H | 0 | CH=CH | H | H | $OC_{18}H_{37}$ | 215–225 |

X = "—" means a single bond.

TABLE 16

| | $R^{53}$ | $R^{54}$ | $R^{55}$ | n | X | $R^{56}$ | $R^{57}$ | $R^{58}$ | Melting point (° C.) |
|---|---|---|---|---|---|---|---|---|---|
| Compound 143 | EtS | H | H | 1 | — | H | H | $OC_{18}H_{37}$ | 149–153 |
| Compound 144 | PrS | H | H | 1 | — | H | H | $OC_{18}H_{37}$ | 132–133.5 |
| Compound 145 | H | MeS | H | 2 | — | H | H | $OC_{18}H_{37}$ | 216–219 |
| Compound 146 | H | EtS | H | 2 | — | H | H | $OC_{18}H_{37}$ | 174–177 |
| Compound 147 | H | PrS | H | 2 | — | H | H | $OC_{18}H_{37}$ | 150–152 |
| Compound 148 | H | $PhCH_2S$ | H | 2 | — | H | H | $OC_{18}H_{37}$ | 178–181 |
| Compound 149 | MeS | H | Et | 2 | — | H | H | $OC_{18}H_{37}$ | 108–110 |

TABLE 16-continued

| | $R^{53}$ | $R^{54}$ | $R^{55}$ | n | X | $R^{56}$ | $R^{57}$ | $R^{58}$ | Melting point (° C.) |
|---|---|---|---|---|---|---|---|---|---|
| Compound 150 | MeS | H | CH$_2$—⊲ | 2 | — | H | H | OC$_{18}$H$_{37}$ | 126–128 |
| Compound 151 | MeS | H | CH$_2$Ph | 2 | — | H | H | OC$_{18}$H$_{37}$ | 127–129 |
| Compound 152 | MeS | H | Me | 3 | O | H | H | OC$_{18}$H$_{33}$ | 102–104 |
| Compound 153 | MeS | H | Me | 0 | CH=CH | H | H | OC$_{18}$H$_{37}$ | 156–157 |

X = "—" means a single bond.

TABLE 17

| | $R^{53}$ | $R^{54}$ | $R^{55}$ | n | X | $R^{56}$ | $R^{57}$ | $R^{58}$ | Melting point (° C.) |
|---|---|---|---|---|---|---|---|---|---|
| Compound 154 | EtS | H | Me | 1 | — | H | H | OC$_{18}$H$_{37}$ | 87–88.5 |
| Compound 155 | PrS | H | Me | 1 | — | H | H | OC$_{18}$H$_{37}$ | 76–80 |
| Compound 156 | MeS | H | CH$_2$CO$_2$H | 2 | — | H | H | OC$_{18}$H$_{37}$ | 154–155 |
| Compound 157 | MeS | H | CH$_2$CONHMe | 2 | — | H | H | OC$_{18}$H$_{37}$ | 142–145 |
| Compound 158 | MeS | H | CH$_2$CONH$_2$ | 2 | — | H | H | OC$_{18}$H$_{37}$ | 149–153 |
| Compound 159 | MeS | | H | H | 2 | — | H | H | 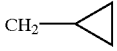 | 204–206 |
| Compound 160 | Me–S(=O)– | | H | H | 2 | — | H | H | OC$_{18}$H$_{37}$ | 188–193 |
| Compound 161 | HO–CH$_2$CH$_2$–S– | | H | Me | 1 | — | H | H | OC$_{18}$H$_{37}$ | 114–117.5 |
| Compound 162 | HO–(CH$_2$)$_3$–S– | | H | Me | 1 | — | H | H | OC$_{18}$H$_{37}$ | 104.5–106.5 |

X = "—" means a single bond.

Example 31

To a solution of 600 mg of Compound 107 dissolved in 4 ml of methylene chloride, was added 2 ml of trifluoroacetic acid. The mixture was stirred for 3.5 hours at room temperature. The solvent was removed under reduced pressure, and subsequently, the residue was dried under reduced pressure, to yield 548 mg of Compound 163 (melting point: 163.5–169.5° C.) (Reaction Scheme (72) described below).

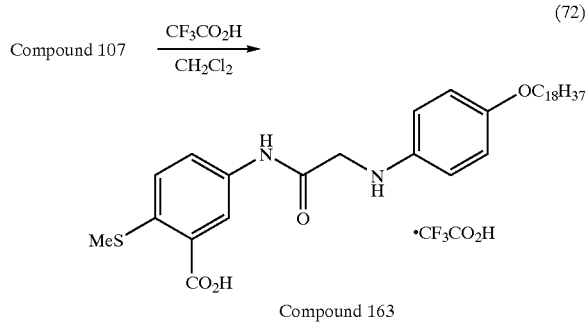

Compound 163

Example 32

Compound 164 (melting point: 151–158° C.) was prepared using Compound 108 in the same procedures as described in Example 31 (Reaction Scheme (73) described below).

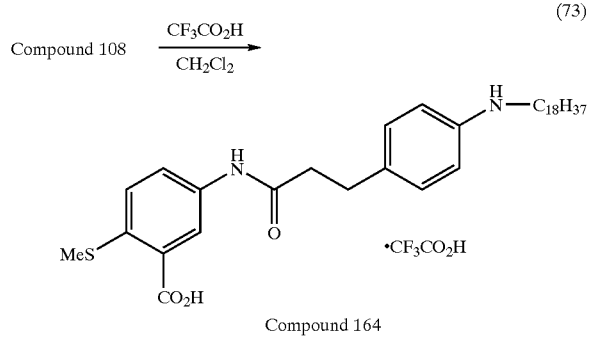

Compound 164

Example 33

Compound 165 to Compound 168 represented by General Formula (74), in which $R^{59}$ and q have the structures shown in Table 18, were prepared using the compounds obtained in the same procedures as described in Example 24, Example 25, Example 16, and Example 17, in the same procedures as described in Example 31. The m/z values of electrospray ionization mass spectrometry (ESIMS) and the Rf values in silica gel thin layer chromatography (produced by Merck & Co., TLC plate silica gel 60F$_{254}$ (0.25 mm), solvent: chloroform—methanol=10:1) of these compounds are also shown in Table 18.

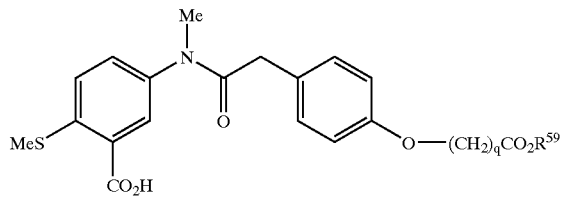

(74)

TABLE 18

| | q | R$^{59}$ | ESIMS: m/z | Rf value |
|---|---|---|---|---|
| Compound 165 | 3 | Me | 432 (MH$^+$) | 0.35 |
| | | | 454 (MNa$^+$) | |
| | | | 430 ((M − H)$^-$) | |
| Compound 166 | 4 | Me | 446 (MH$^+$) | 0.35 |
| | | | 468 (MNa$^+$) | |
| | | | 444 ((M − H)$^-$) | |
| Compound 167 | 4 | Et | 460 (MH$^+$) | 0.35 |
| | | | 482 (MNa$^+$) | |
| | | | 458 ((M − H)$^-$) | |
| Compound 168 | 6 | Me | 488 (MH$^+$) | 0.35 |
| | | | 510 (MNa$^+$) | |
| | | | 486 ((M − H)$^-$) | |

Experimental Example 1

According to the method described in a document (*Cell Growth & Differentiation*, vol. 7, pp. 213–221, 1996), the following tests were carried out.

NIH3T3 cells in which Flt-1 was forced to be expressed were seeded on a 24-well collagen-coated plate (7×10$^4$/well), and were cultured in Dulbecco's modified Eagle's medium (DMEM) including 10% bovine serum and 200 μg/ml of Geneticin G418, for 24 hours at 37° C. under an atmosphere of 5% carbon dioxide gas. The cells were preincubated in Buffer A (including 10 mM HEPES (N-2-hydroxyethylpiperazine-N'-2-ethanesulfonic acid) and 0.1% BSA (bovine serum albumin) in DMEM), for 30 minutes at 4° C. Subsequently, the medium was replaced with Buffer B (including 10 mM HEPES and 0.5% BSA in DMEM). A test solution prepared by dissolving each of the test compounds shown in Table 19 in dimethylsulfoxide and subsequently diluting the solution into a prescribed concentration with Buffer B, and ($^{125}$I)-VEGF (the final concentration was set to 25 pM) were added thereto. Binding reaction was carried out for 90 minutes at 40. After completion of the reaction, the cells were washed three times with ice-cooled Buffer A. Subsequently, 0.5 ml of 0.5M NaOH were added to each well, and the cells were lysed in 30 minutes at room temperature. The radioactivity of the lysed cells in each well was measured by means of a gamma counter, and a total binding quantity of ($^{125}$I)-VEGF was calculated. Nonspecific binding quantity of ($^{125}$I)-VEGF was measured by competition assay in the presence of 10 nM non-labeled VEGF. The specific binding quantity of ($^{125}$I)-VEGF was calculated from the difference between the total binding quantity of ($^{125}$I)-VEGF and nonspecific binding quantity of ($^{125}$I)-VEGF.

The binding inhibition index of the test compounds was calculated by the following equation.

$$\text{Binding inhibition index (\%)} = \left(1 - \frac{\text{Specific binding quantity of }(^{125}I)\text{-}VEGF\text{ of the group with an addition of test compounds}}{\text{Specific binding quantity of }(^{125}I)\text{-}VEGF\text{ of the control group}}\right) \times 100$$

From this value, a concentration of 50% binding inhibition (IC$_{50}$) of the test compound was calculated. The results are shown in Table 19.

TABLE 19

| | IC$_{50}$ (μM) |
|---|---|
| Compound 27 | 0.68 |
| Compound 28 | 0.71 |
| Compound 113 | 0.28 |
| Compound 114 | 0.42 |

Experimental Example 2

Test on each of the test compounds shown in Table 20 and Table 21 was carried out employing NIH3T3 cells in which KDR was forced to be expressed, in the same manner as described in Experimental Example 1 described above. The results are shown in Table 20 and Table 21.

TABLE 20

| | IC$_{50}$ (μM) |
|---|---|
| Compound 27 | 0.51 |
| Compound 28 | 0.42 |
| Compound 29 | 1.19 |
| Compound 31 | 1.23 |
| Compound 32 | 0.93 |
| Compound 33 | 0.26 |
| Compound 34 | 0.34 |
| Compound 35 | 0.20 |
| Compound 36 | 1.27 |
| Compound 38 | 0.71 |
| Compound 41 | 0.37 |
| Compound 42 | 0.45 |
| Compound 43 | 0.66 |
| Compound 44 | 0.91 |
| Compound 45 | 0.76 |
| Compound 46 | 0.40 |
| Compound 47 | 0.94 |

TABLE 21

| | $IC_{50}$ ($\mu M$) |
|---|---|
| Compound 113 | 0.08 |
| Compound 114 | 0.34 |
| Compound 115 | 0.15 |
| Compound 116 | 0.16 |
| Compound 117 | 0.32 |
| Compound 118 | 1.58 |
| Compound 119 | 0.29 |
| Compound 120 | 0.44 |
| Compound 127 | 1.16 |
| Compound 130 | 0.23 |
| Compound 131 | 0.31 |
| Compound 132 | 1.66 |
| Compound 133 | 0.16 |
| Compound 134 | 0.12 |
| Compound 135 | 0.45 |
| Compound 136 | 0.40 |
| Compound 137 | 0.46 |
| Compound 138 | 0.43 |
| Compound 143 | 0.76 |
| Compound 145 | 1.29 |
| Compound 146 | 0.63 |
| Compound 147 | 0.57 |
| Compound 148 | 0.93 |
| Compound 149 | 0.14 |
| Compound 150 | 0.59 |
| Compound 151 | 0.80 |
| Compound 153 | 0.25 |
| Compound 154 | 0.50 |
| Compound 155 | 0.67 |
| Compound 161 | 1.30 |
| Compound 162 | 1.16 |
| Compound 163 | 0.41 |
| Compound 164 | 0.57 |

Industrial Applicability

It is believed that the compounds of the present invention inhibit angiogenesis by inhibiting VEGF-dependent proliferation of vascular endothelial cells and suppress vascular hyperpermeability due to VEGF.

Therefore, the compounds of the present invention are expected to be therapeutic agents for the diseases in which angiogenesis is involved and which are induced by VEGF, such as diabetic retinopathy, chronic rheumatism, and solid tumors. In addition, in the compounds of the present invention, suppressing effects on pathologic symptoms in which vascular hyperpermeability induced by VEGF is involved, such as cerebral edema upon ischemia reperfusion injury, are expected.

What is claimed is:

1. An aminobenzoic acid derivative represented by Formula (1) as follows:

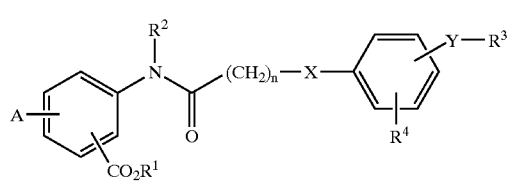

(1)

{in Formula (1), $R^1$ represents a hydrogen atom or a $C_{1-6}$alkyl group;

$R^2$ represents a hydrogen atom, a $C_{1-6}$alkyl group, a $C_{3-8}$ cycloalkyl $C_{1-3}$alkyl group, a phenyl $C_{1-3}$alkyl group, a group represented by $CH_2CO_2R^5$ (wherein $R^5$ represents a hydrogen atom or a $C_{1-6}$alkyl group), or a group represented by $CH_2CON(R^6)R^7$ (wherein $R^6$ and $R^7$ independently represent a hydrogen atom or a $C_{1-6}$alkyl group);

$R^3$ represents a $C_{8-25}$alkyl group, a group represented by $(CH_2)_pCO_2R^{11}$ (where in p is an integer of 1 to 20, and $R^{11}$ represents a hydrogen atom or a $C_{1-6}$alkyl group), or a group represented by $(CH_2)_3CONHCH$ $(R^{12})$CONHR$^1$ (wherein $R^{12}$ represents a hydrogen atom or a group represented by $CH_2CO_2R^{14}$ group (wherein $R^{14}$ represents a hydrogen atom or a $C_{1-6}$alkyl group), and $R^{13}$ represents a $C_{1-20}$ alkyl group);

$R^4$ represents a hydrogen atom or a group represented by $OR^9$ or $CO_2R^{10}$ (wherein $R^9$ and $R^{10}$ independently represent a hydrogen atom or a $C_{1-6}$alkyl group), A represents a group represented by $S(O)_qR^{15}$ (wherein q is 0, 1, or 2, $R^{15}$ represents a $C_{1-6}$alkyl group, a phenyl $C_{1-3}$alkyl group, or a group represented by $(CH_2)_mOR^{16}$ (wherein m is 2 or 3, and $R^{16}$ represents a hydrogen atom or a methoxymethyl group)), a group represented by Formula (2) as follows:

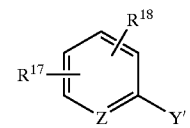

(2)

(in the formula, $R^{17}$ represents a hydrogen atom or a group represented by $CO_2R^{19}$, $CH_2CO_2R^{20}$, $CH_2CH_2CO_2R^{21}$, or $CH=CHCO_2R^{22}$ (wherein $R^{19}$, $R^{20}$, $R^{21}$, and $R^{22}$ independently represent a hydrogen atom or a $C_{1-6}$alkyl group), $R^{18}$ represents a hydrogen atom or a group represented by $CO_2R^{23}$ (wherein $R^{23}$ represents a hydrogen atom or a $C_{1-6}$alkyl group), Y' represents O, S, or $NR^{24}$ (wherein $R^{24}$ represents a hydrogen atom or a $C_{1-6}$alkyl group), and Z represents CH or N), or a group represented by Formula (3) as follows:

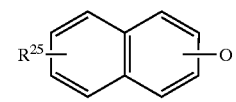

(3)

(in the formula, $R^{25}$ represents a hydrogen atom or a group represented by $CO_2R^{26}$ (wherein $R^{26}$ represents a hydrogen atom or a $C_{1-6}$alkyl group));

X represents O, a single bond, or a group represented by $NR^{27}$ (wherein $R^{27}$ represents a hydrogen atom or a t-butoxycarbonyl group);

Y represents O, CONH, NHCO, or a group represented by $NR^{28}$ (wherein $R^{28}$ represents a hydrogen atom or a t-butoxycarbonyl group, with the proviso that when Y represents NHCO, A is not represented by Formula (2) described above); and n is an integer of 0 to 15} or a pharmaceutically acceptable salt of the same.

2. The aminobenzoic acid derivative or pharmaceutically acceptable salt of the same, according to claim 1, wherein in Formula (1), A represents a group represented by Formula (2) (in the formula, $R^{17}$, $R^{18}$, Y', and Z have the same meanings as described above), or a group represented by Formula (3) (in the formula, $R^{25}$ has the same meaning as described above; and Y represents O, CONH, or a group represented by $NR^{28}$ (wherein $R^{28}$ has the same meaning as described above).

3. The aminobenzoic acid derivative or pharmaceutically acceptable salt of the same, according to claim 2, wherein the Formula (1) described above is represented by Formula (4) as follows:

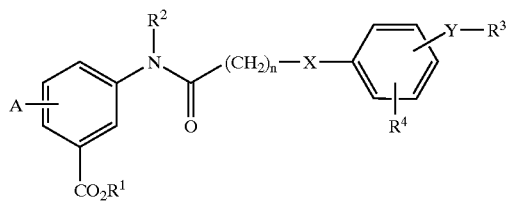

(4)

in Formula (4), $R^1$ represents a hydrogen atom or a $C_{1-6}$alkyl group; $R^2$ represents a hydrogen atom or a $C_{1-6}$alkyl group; $R^3$ represents a $C_{8-25}$alkyl group; $R^4$ represents a hydrogen atom; A represents a group represented by Formula (2) (in the formula, $R^{17}$, $R^{18}$, Y', and Z have the same meanings as described above), or a group represented by Formula (3) (in the formula, $R^{25}$ has the same meaning as described above); and X represents O or a single bond; Y represents O; and n is an integer of 1 to 11.

4. The aminobenzoic acid derivative or pharmaceutically acceptable salt of the same, according to claim 3, wherein in Formula (4), A represents a group represented by Formula (5) as follows:

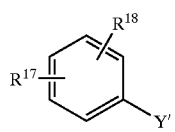

(5)

(in the formula, $R^{17}$, $R^{18}$, and Y' have the same meanings as described above).

5. The aminobenzoic acid derivative or pharmaceutically acceptable salt of the same, according to claim 4, wherein in Formula (5), $R^{17}$ represents a group represented by $CO_2R^{19}$, (wherein $R^{19}$ represents a hydrogen atom or a $C_{1-6}$alkyl group), and $R^{18}$ represents a hydrogen atom.

6. The aminobenzoic acid derivative or pharmaceutically acceptable salt of the same, according to claim 5, wherein in Formula (4) $R^3$ represents a $C_{14-22}$alkyl group.

7. The aminobenzoic acid derivative or pharmaceutically acceptable salt of the same, according to claim 3, wherein Formula (4) is represented by Formula (6) as follows:

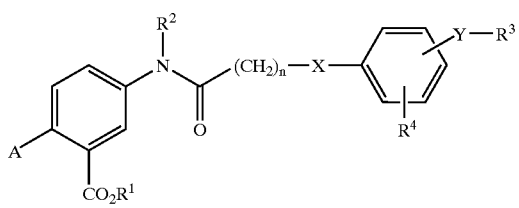

(6)

in Formula (6), $R^1$ represents a hydrogen atom or a $C_{1-6}$alkyl group; $R^2$ represents a hydrogen atom or a $C_{1-6}$alkyl group; $R^3$ represents a $C_{18}$alkyl group; $R^4$ represents a hydrogen atom; A represents a group represented by Formula (5) as follows:

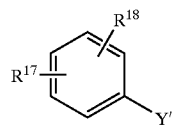

(5)

(in the formula, $R^{17}$ represents a group represented by $CO_2R^{19}$ (wherein $R^{19}$ represents a hydrogen atom or a $C_{1-6}$alkyl group), $R^{18}$ represents a hydrogen atom, Y' represents O, S, or $NR^{24}$ (wherein $R^{24}$ represents a hydrogen atom or a $C_{1-6}$alkyl group)), X represents O or a single bond; Y represents O; and n is an integer of 1 to 11.

8. The aminobenzoic acid derivative or pharmaceutically acceptable salt of the same, according to claim 7, wherein in Formula (6), X represents a single bond and n is 2.

9. The aminobenzoic acid derivative or pharmaceutically acceptable salt of the same, according to claim 1, wherein in Formula (1), A represents a group represented by $S(O)_qR^{15}$ (wherein q and $R^{15}$ have the same meanings as described above).

10. The aminobenzoic acid derivative or pharmaceutically acceptable salt of the same, according to claim 9, wherein Formula (1) is represented by Formula (4) as follows:

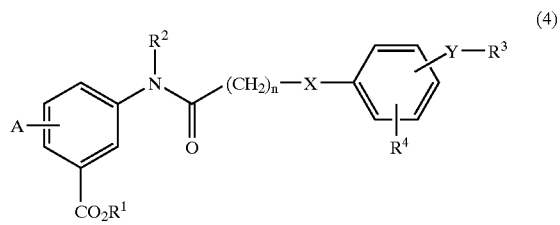

(4)

in Formula (4), $R^1$ represents a hydrogen atom or a $C_{1-6}$alkyl group; $R^2$ represents a hydrogen atom, a $C_{1-6}$alkyl group, a $_{3-8}$cycloalkyl $C_{1-3}$alkyl group, a phenyl $C_{1-3}$alkyl group, a group represented by $CH_2CO_2R^5$ (wherein $R^5$ represents a hydrogen atom or a $C_{1-6}$alkyl group), or a group represented by $CH_2CON(R^6)R^7$ (wherein $R^6$ and $R^7$ independently represent a hydrogen atom or a $C_{1-6}$alkyl group);

$R^3$ represents a $C_{8-25}$alkyl group, a group represented by $(CH_2)_pCO_2R^{11}$ (wherein p is an integer of 1 to 20, and $R^{11}$ represents a hydrogen atom or a $C_{1-6}$alkyl group), or a group represented by $(CH_2)_3CONHCH$ $(R^{12})$ $CONHR^{13}$ (wherein $R^{12}$ represents a hydrogen atom or a group represented by $CH_2CO_2R^{14}$ group (wherein $R^{12}$ represents a hydrogen atom or a $C_{1-6}$alkyl group), and $R^{13}$ represents a $C_{1-20}$ alkyl group);

$R^4$ represents a hydrogen atom or a group represented by $OR^9$ or $CO_2R^{10}$ (wherein $R^9$ and $R^{10}$ independently represent a hydrogen atom or a $C_{1-6}$alkyl group);

A represents a group represented by $SR^{15}$ (wherein $R^{15}$ represents a $C_{1-6}$alkyl group);

X represents O, a single bond, or a group represented by $NR^{27}$ (wherein $R^{27}$ represents a hydrogen atom or a t-butoxycarbonyl group);

Y represents O, CONH, NHCO, or a group represented by $NR^{28}$ (wherein $R^{28}$ represents a hydrogen atom or a t-butoxycarbonyl group); and n is an integer of 0 to 15.

11. The aminobenzoic acid derivative or pharmaceutically acceptable salt of the same, according to claim 10, wherein in Formula (4), $R^3$ represents a $C_{14-22}$alkyl group.

12. The aminobenzoic acid derivative or pharmaceutically acceptable salt of the same, according to claim 9, wherein Formula (4) is represented by Formula (6) as follows:

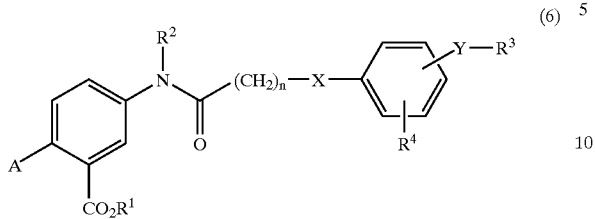

(6)

in Formula (6), $R^1$ represents a hydrogen atom or a $C_{1-6}$alkyl group; $R^2$ represents a hydrogen atom, a $C_{1-6}$alkyl group, a $C_{3-8}$cycloalkyl $C_{1-3}$alkyl group, a phenyl $C_{1-3}$alkyl group, a group represented by $CH_2CO_2R^5$ (wherein $R^5$ represents a hydrogen atom or a $C_{1-6}$alkyl group), or a group represented by $CH_2CON(R^6)R^7$ (wherein $R^6$ and $R^7$ independently represent a hydrogen atom or a $C_{1-6}$alkyl group);

$R^3$ represents a $C_{1-8}$alkyl group;

$R^4$ represents a hydrogen atom or a group represented by $OR^9$ or $CO_2R^{10}$ (wherein $R^9$ and $R^{10}$ independently represent a hydrogen atom or a $C_{1-6}$alkyl group);

A represents a group represented by SR (wherein $R^{15}$ represents a $C_{1-6}$alkyl group);

X represents O, a single bond, or a group represented by $NR^{27}$ (wherein $R^{27}$ represents a hydrogen atom or a t-butoxycarbonyl group);

Y represents O, CONH, NHCO, or a group represented by $NR^{28}$ (wherein $R^{28}$ represents a hydrogen atom or a t-butoxycarbonyl group); and n is an integer of 0 to 15.

13. The aminobenzoic acid derivative or pharmaceutically acceptable salt of the same, according to claim 12, wherein in Formula (6), $R^2$ represents a hydrogen atom or a $C_{1-6}$alkyl group; $R^4$ represents a hydrogen atom; X represents a single bond; Y represents O; and n is 1 or 2.

* * * * *